US006949264B1

(12) United States Patent
McGrew et al.

(10) Patent No.: US 6,949,264 B1
(45) Date of Patent: Sep. 27, 2005

(54) NUTRACEUTICALS OR NUTRITIONAL SUPPLEMENTS AND METHOD OF MAKING

(75) Inventors: Gordon N. McGrew, Evanston, IL (US); David G. Barkalow, Deerfield, IL (US); Sonya S. Johnson, LaGrange Highlands, IL (US); David W. Record, River Forest, IL (US); Mansukh M. Patel, Downers Grove, IL (US); Jack D. Nimz, Wauconda, IL (US); Steven E. Zibell, Tinley Park, IL (US); Robert J. Yatka, Orland Park, IL (US); Michael J. Greenberg, Northbrook, IL (US); Rebecca A. Aumann, Chicago, IL (US); Daniel J. Zyck, North Riverside, IL (US); Daniel J. Sitler, Woodridge, IL (US); Jeffrey S. Hook, Lockport, IL (US); James R. Maxwell, Chicago, IL (US); Michael A. Reed, Merrillville, IN (US); Victor V. Gudas, Oak Lawn, IL (US); Philip G. Schnell, Downers Grove, IL (US); Henry T. Tyrpin, Palos Park, IL (US); Michael P. Russell, Evergreen Park, IL (US); David L. Witkewitz, Bridgeview, IL (US); Joo H. Song, Chicago, IL (US); Donald J. Townsend, Moores Hill, IN (US); Donald A. Seielstad, Frankfurt, IL (US); Ronald L. Ream, Plano, IL (US); Christine L. Corriveau, Orland Park, IL (US); William J. Wokas, Bolingbrook, IL (US); Thomas M. Tongue, Joliet, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/621,780

(22) Filed: Jul. 21, 2000

Related U.S. Application Data

(63) Continuation of application No. PCT/US99/29792, filed on Dec. 14, 1999, which is a continuation-in-part of application No. 09/389,211, filed on Sep. 2, 1999, now abandoned, and a continuation-in-part of application No. 09/286,818, filed on Apr. 6, 1999, and a continuation-in-part of application No. 09/308,972, filed as application No. PCT/US96/18977 on Nov. 27, 1996, now Pat. No. 6,165,516.

(60) Provisional application No. 60/112,389, filed on Dec. 15, 1998.

(51) Int. Cl.$^7$ ............................ A23G 3/30; A61K 9/68
(52) U.S. Cl. ............................ 426/3; 424/48; 424/440; 426/5
(58) Field of Search .................. 426/3, 5, 6; 424/48, 424/440

(56) References Cited

U.S. PATENT DOCUMENTS

| | | | |
|---|---|---|---|
| 1,298,670 A | 4/1919 | Cramer | |
| 1,629,461 A | 5/1927 | Berg et al. | |
| 2,892,753 A | 6/1959 | Schmidt | |
| 2,990,328 A | 6/1961 | Lincoln | |
| 3,011,949 A | 12/1961 | Bilotti | |
| 3,029,189 A | 4/1962 | Hardy et al. | |
| 3,047,461 A | 7/1962 | Hardy et al. | |
| 3,075,884 A | 1/1963 | Bilotti et al. | |
| 3,196,172 A | 7/1965 | Wright, Jr. et al. | |
| 3,308,022 A | 3/1967 | Cummings et al. | |
| 3,498,964 A | 3/1970 | Hayashi | |
| 3,554,767 A | 1/1971 | Daum | |
| 3,590,057 A | 6/1971 | Susuki et al. | |
| 3,845,217 A | 10/1974 | Ferno et al. | 426/3 |
| 3,877,468 A | 4/1975 | Lichtneckert et al. | 131/2 |
| 3,901,248 A | 8/1975 | Lichtneckert et al. | 131/2 |
| 3,995,064 A | 11/1976 | Ehrgott et al. | 426/3 |
| 4,154,814 A | 5/1979 | Hand et al. | |
| 4,238,475 A | 12/1980 | Witzel et al. | 424/48 |
| 4,238,510 A | 12/1980 | Cherukuri et al. | 426/5 |
| 4,250,195 A | 2/1981 | Cherukuri et al. | |
| 4,283,408 A | 8/1981 | Hirata et al. | 424/270 |
| 4,317,838 A | 3/1982 | Cherukuri et al. | 426/5 |
| 4,374,858 A | 2/1983 | Glass et al. | |
| 4,378,374 A | 3/1983 | Reggio et al. | |

(Continued)

FOREIGN PATENT DOCUMENTS

| | | |
|---|---|---|
| DE | 43 42 568 A1 | 6/1994 |
| EP | 0 202 819 A2 | 11/1986 |
| EP | 0 217 109 A2 | 4/1987 |
| EP | 0 221 850 | 5/1987 |
| EP | 0 239 541 A2 | 9/1987 |

(Continued)

OTHER PUBLICATIONS

Brochure for "Minerals Technologies Specialty Minerals", 1998, 19 pages.

Akitoshi et al., Abstract "Acceleration of Transdermal Absorption of Pharmaceuticals by Essential Oils and Organic Solvents," Chem. Abst., 112:125228t, 1990.

(Continued)

*Primary Examiner*—Arthur L Corbin
(74) *Attorney, Agent, or Firm*—Steven P. Shurtz; Brinks Hofer Gilson & Lione

(57) ABSTRACT

A method for producing a chewing gum with a controlled release active agent, as well as the chewing gum so produced, is obtained by physically modifying the release properties of the active agent, such as a nutraceutical or nutritional supplement, by coating and drying. The active agent is coated by encapsulation, partially coated by agglomeration, entrapped by absorption, or treated by multiple steps of encapsulation, agglomeration, and absorption. The coated active agent is preferably then co-dried and particle sized to produce a release-modified active agent for use in chewing gum. The active agent may also be used in a coating on a chewing gum product, as part of a rolling compound applied to the chewing gum product, or as a part of the liquid in a liquid-center chewing gum product.

42 Claims, No Drawings

U.S. PATENT DOCUMENTS

| | | | |
|---|---|---|---|
| 4,386,063 A | 5/1983 | Boden | |
| 4,386,106 A | 5/1983 | Merritt et al. | |
| 4,400,372 A | 8/1983 | Muhker et al. | |
| 4,446,135 A | 5/1984 | Fountaine | 424/154 |
| 4,452,821 A | 6/1984 | Gergely | 426/5 |
| 4,459,311 A | 7/1984 | DeTora et al. | 426/3 |
| 4,474,749 A | 10/1984 | Kruppa | |
| 4,512,968 A | 4/1985 | Komiyama et al. | 424/48 |
| 4,533,556 A | 8/1985 | Piccolo et al. | |
| 4,555,407 A | 11/1985 | Kramer et al. | 426/5 |
| 4,563,345 A | 1/1986 | Arrick | |
| 4,639,368 A | 1/1987 | Niazi et al. | 424/48 |
| 4,647,450 A | 3/1987 | Peters et al. | |
| 4,711,774 A | 12/1987 | Denick, Jr. et al. | 424/48 |
| 4,716,033 A | 12/1987 | Denick, Jr. | 424/48 |
| 4,737,366 A | 4/1988 | Gergely et al. | 426/5 |
| 4,753,800 A | 6/1988 | Mozda | |
| 4,753,805 A | 6/1988 | Cherukuri et al. | 426/5 |
| 4,755,389 A | 7/1988 | Jones et al. | |
| 4,758,424 A | 7/1988 | Denick, Jr. et al. | 424/48 |
| 4,822,597 A | 4/1989 | Faust et al. | |
| 4,822,816 A | 4/1989 | Markham | |
| 4,828,820 A | 5/1989 | Glass et al. | |
| 4,832,994 A | 5/1989 | Fey | |
| 4,835,162 A | 5/1989 | Abood | |
| 4,849,227 A | 7/1989 | Cho | |
| 4,853,212 A | 8/1989 | Faust et al. | |
| 4,867,989 A | 9/1989 | Silva et al. | |
| 4,882,152 A | 11/1989 | Yang et al. | 424/440 |
| 4,894,234 A | 1/1990 | Sharma et al. | 424/440 |
| 4,908,211 A | 3/1990 | Paz | |
| 4,908,212 A | 3/1990 | Kwon et al. | |
| 4,929,447 A | 5/1990 | Yang | |
| 4,929,508 A | 5/1990 | Sharma et al. | 424/439 |
| 4,933,184 A | 6/1990 | Tsuk | |
| 4,935,242 A | 6/1990 | Sharma et al. | 424/439 |
| 4,938,963 A | 7/1990 | Parnell | |
| 4,944,949 A | 7/1990 | Story et al. | |
| 4,963,369 A | 10/1990 | Song et al. | 426/5 |
| 4,968,511 A | 11/1990 | D'Amelia et al. | 426/6 |
| 4,968,716 A | 11/1990 | Markham | |
| 4,971,079 A | 11/1990 | Talapin et al. | 131/359 |
| 4,971,787 A | 11/1990 | Cherukuri et al. | 424/48 |
| 4,971,806 A * | 11/1990 | Cherukuri | 426/5 |
| 4,975,270 A | 12/1990 | Kehoe | 424/48 |
| 4,978,537 A | 12/1990 | Song | 426/5 |
| 4,997,659 A | 3/1991 | Yatka et al. | 426/3 |
| 5,013,716 A | 5/1991 | Cherukuri et al. | 514/23 |
| 5,015,464 A | 5/1991 | Strobridge | |
| 5,045,325 A | 9/1991 | Lesko et al. | 426/5 |
| 5,070,085 A | 12/1991 | Markham | |
| 5,110,608 A | 5/1992 | Cherukuri | |
| 5,124,156 A | 6/1992 | Shibata et al. | |
| 5,126,151 A | 6/1992 | Bodor et al. | |
| 5,139,787 A | 8/1992 | Broderick et al. | |
| 5,139,794 A | 8/1992 | Patel et al. | |
| 5,154,927 A | 10/1992 | Song et al. | |
| 5,156,842 A | 10/1992 | Mulligan | |
| 5,179,122 A | 1/1993 | Greene et al. | |
| 5,182,099 A | 1/1993 | Jonsson et al. | |
| 5,229,137 A | 7/1993 | Wolfe | 424/687 |
| 5,244,670 A | 9/1993 | Upson et al. | 424/439 |
| 5,284,657 A | 2/1994 | Lu et al. | |
| 5,286,500 A | 2/1994 | Synosky et al. | 426/3 |
| 5,294,433 A | 3/1994 | Singer et al. | |
| 5,294,449 A | 3/1994 | Greenberg | |
| 5,340,566 A | 8/1994 | Curtis et al. | |
| 5,378,131 A | 1/1995 | Greenberg | |
| 5,380,530 A | 1/1995 | Hill | |
| 5,380,535 A | 1/1995 | Geyer et al. | |
| 5,397,580 A | 3/1995 | Song et al. | 426/5 |
| 5,410,028 A | 4/1995 | Asami et al. | |
| 5,419,919 A | 5/1995 | Song et al. | 426/5 |
| 5,425,961 A * | 6/1995 | Yatka et al. | 426/3 |
| 5,431,929 A * | 7/1995 | Yatka et al. | 426/3 |
| 5,433,960 A | 7/1995 | Meyers | 426/5 |
| 5,445,834 A | 8/1995 | Burger et al. | |
| 5,455,286 A | 10/1995 | Amidon et al. | |
| 5,456,677 A | 10/1995 | Spector | 604/290 |
| 5,487,902 A | 1/1996 | Andersen et al. | 426/3 |
| 5,488,962 A | 2/1996 | Perfetti | |
| 5,494,685 A | 2/1996 | Tyrpin et al. | 426/5 |
| 5,496,541 A | 3/1996 | Cutler | |
| 5,512,306 A | 4/1996 | Carlsson et al. | |
| 5,523,097 A | 6/1996 | Song et al. | 426/3 |
| 5,534,272 A | 7/1996 | Bernstein | |
| 5,536,511 A | 7/1996 | Yatka | |
| 5,543,160 A | 8/1996 | Song et al. | 426/3 |
| 5,554,380 A | 9/1996 | Cuca et al. | |
| 5,569,477 A | 10/1996 | Nesbitt | 426/5 |
| 5,571,528 A | 11/1996 | Lee et al. | |
| 5,571,543 A | 11/1996 | Song et al. | 426/5 |
| 5,576,344 A | 11/1996 | Sandler et al. | 514/427 |
| 5,578,336 A * | 11/1996 | Monte | 426/72 |
| 5,580,590 A | 12/1996 | Hartman | 426/3 |
| 5,582,855 A | 12/1996 | Cherukuri et al. | 426/5 |
| 5,585,110 A | 12/1996 | Kalili et al. | |
| 5,593,685 A | 1/1997 | Bye et al. | |
| 5,601,858 A | 2/1997 | Manshukhani | |
| 5,605,698 A | 2/1997 | Ueno | |
| 5,607,697 A | 3/1997 | Alkire et al. | 424/495 |
| 5,618,517 A | 4/1997 | Miskewitz | |
| 5,628,986 A | 5/1997 | Sanker et al. | |
| 5,629,013 A | 5/1997 | Upson et al. | 424/441 |
| 5,629,026 A | 5/1997 | Davis | 424/686 |
| 5,629,035 A | 5/1997 | Miskewitz | |
| 5,645,853 A | 7/1997 | Winston et al. | |
| 5,651,987 A | 7/1997 | Fuisz | 424/488 |
| 5,656,652 A | 8/1997 | Davis | 514/400 |
| 5,665,386 A | 9/1997 | Benet et al. | |
| 5,665,406 A | 9/1997 | Reed et al. | |
| 5,667,802 A | 9/1997 | Grimberg | |
| 5,693,334 A | 12/1997 | Miskewitz | |
| 5,698,215 A | 12/1997 | Kalili et al. | |
| 5,702,687 A | 12/1997 | Miskewitz | |
| 5,711,961 A | 1/1998 | Reiner et al. | 424/441 |
| 5,716,928 A | 2/1998 | Benet et al. | |
| 5,736,175 A | 4/1998 | Cea et al. | |
| 5,744,164 A | 4/1998 | Chauffard et al. | |
| 5,753,255 A | 5/1998 | Chavkin et al. | |
| 5,756,074 A | 5/1998 | Ascione et al. | |
| 5,800,847 A | 9/1998 | Song et al. | 426/3 |
| 5,824,291 A | 10/1998 | Howard | |
| 5,834,002 A | 11/1998 | Athanikar | 424/440 |
| 5,846,557 A | 12/1998 | Eisenstadt et al. | |
| 5,854,267 A | 12/1998 | Berlin et al. | 514/370 |
| 5,858,383 A | 1/1999 | Precopio | 424/405 |
| 5,858,412 A | 1/1999 | Staniforth et al. | 424/489 |
| 5,858,413 A | 1/1999 | Jettka et al. | 424/682 |
| 5,858,423 A | 1/1999 | Yajima et al. | 426/7 |
| 5,866,179 A | 2/1999 | Testa | 426/3 |
| 5,877,173 A | 3/1999 | Olney et al. | 514/217 |
| 5,882,702 A | 3/1999 | Abdel-Malik et al. | |
| 5,889,028 A | 3/1999 | Sandborn et al. | 514/343 |
| 5,889,029 A | 3/1999 | Rolf | 514/343 |
| 5,897,891 A | 4/1999 | Godfrey | 426/74 |
| 5,900,230 A | 5/1999 | Cutler | |
| 5,912,007 A | 6/1999 | Pan et al. | 424/440 |
| 5,912,030 A | 6/1999 | Huziinec et al. | |
| 5,916,606 A | 6/1999 | Record et al. | 426/3 |
| 5,922,346 A | 7/1999 | Hersh | |

| | | | |
|---|---|---|---|
| 5,922,347 A | 7/1999 | Häusler et al. | 424/441 |
| 5,928,664 A | 7/1999 | Yang et al. | 424/440 |
| 5,958,380 A | 9/1999 | Winston et al. | |
| 5,958,472 A | 9/1999 | Robinson et al. | |
| 5,980,955 A | 11/1999 | Greenberg et al. | 426/5 |
| 5,989,588 A | 11/1999 | Korn et al. | 424/465 |
| 6,024,988 A | 2/2000 | Ream et al. | 426/3 |
| 6,066,342 A | 5/2000 | Gurol et al. | 424/637 |
| 6,077,524 A | 6/2000 | Bolder et al. | |
| 6,090,412 A | 7/2000 | Hashimoto et al. | 424/490 |
| 6,165,516 A | 12/2000 | Gudas et al. | |
| 6,200,604 B1 | 3/2001 | Pather et al. | |
| 6,290,985 B2 | 9/2001 | Ream et al. | |

FOREIGN PATENT DOCUMENTS

| | | |
|---|---|---|
| EP | 0 273 809 B1 | 12/1987 |
| EP | 0 371 584 A2 | 6/1990 |
| FR | 2 345 938 | 10/1977 |
| FR | 2 635 441 | 2/1990 |
| FR | 2 706 771 | 6/1993 |
| GB | 0 934 596 | 8/1963 |
| GB | 0 963 518 | 7/1964 |
| GB | 1 489 832 | 10/1977 |
| GB | 2 181 646 A | 4/1987 |
| IT | 01273487 | 7/1997 |
| IT | 01293655 | 3/1999 |
| JP | 86-242561 | 10/1986 |
| JP | 91-112450 | 5/1991 |
| JP | 91-251533 | 11/1991 |
| JP | 94-303911 | 11/1994 |
| JP | 96-19370 | 1/1996 |
| KR | 94-2868 | 4/1994 |
| WO | WO 84/02271 | 6/1984 |
| WO | WO 90/12511 | 11/1990 |
| WO | WO 90/12583 | 11/1990 |
| WO | WO 92/06680 | 4/1992 |
| WO | 92/08371 * | 5/1992 |
| WO | 93/12666 * | 7/1993 |
| WO | WO 95/00038 | 1/1995 |
| WO | WO 95/00039 | 1/1995 |
| WO | WO 95/10290 | 4/1995 |
| WO | WO 96/00070 | 1/1996 |
| WO | WO 96/03975 | 2/1996 |
| WO | WO 97/21424 | 6/1997 |
| WO | WO 97/24036 | 6/1997 |
| WO | WO 98/23165 | 6/1998 |
| WO | WO 98/23166 | 6/1998 |
| WO | WO 98/23167 | 6/1998 |
| WO | WO 99/27798 | 6/1999 |
| WO | WO 99/33352 | 7/1999 |
| WO | WO 99/44436 | 9/1999 |
| WO | WO 00/13523 | 3/2000 |
| WO | WO 00/35296 | 6/2000 |
| WO | WO 00/35298 | 6/2000 |
| WO | WO 00/38532 | 7/2000 |
| WO | WO 02/13781 A1 | 2/2002 |

OTHER PUBLICATIONS

Bradford, A Rapid and Sensitive Method for the Quantification of Microgram Quantities of Protein Utilizing the Principle of Protein–Dye Binding, Analytical Biochemistry, 72:248–254 (1976).

Nielsen et al., P–Glycoprotein as Multidrug Transporter: A Critical Review of Current Multidrug Resistant Cell Lines, Chimica et Biophysica Acta., 1139:169–183 (1992).

Adams, M.W., d–Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical Technology, Paris, Jun. 2–4, 1992.

Beckett, A. H. et al., "Buccal absorption of basic drus and its application as an in viov model of passive drug transfer through lipid membranes", (1967) *J. Pharma. Pharmac.*, Suppl. No. 19, pp. 31S–41S.

Chang, Tammy et al., "The Effect of Water–Soluble Vitamin E on Cyclosporine Pharmacokinetics in Healthy Volunteers," Abstract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) *Clin. Pharmacol. Ther.* 52:453–457.

Kronbach, Thomas et al.; "Oxidation of Midazolam and Triazolam by Human Liver Cytochrome P450IIIA4" (1989) *Molec. Pharm.* 36:89–96.

Lalka et al.; "The Hepatic First–Pass Metabolism of Problematic Drugs" (1993) *J. Clin. Pharmacol.* 33:657–669.

Lum et al.; "Clinical Trials of Modulation of Multidrug Resistance. Pharmacokinetic and Pharmacodynamic Considerations" (1993) *Cancer* 72:3502–3514.

Muranishi, Shozo; "Absorption Enhancers" (1990) *Crit. Rev. Ther. Drug Carrier Sys.,* 7:1–33.

Somberg et al.; "The Clinical Implications of First–Pass Metabolism: Treatment Strategies for the 1990's" (1993) *J. Clin. Pharmacol.* 33:670–673.

Tam, Yun K.; "Individual Variation in First–Pass Metabolism" (1993) *Clin. Pharmacokinet.* 25:300–328.

Van Hoogdalem et al.; "Intestinal Drug Absorption Enhancement: An Overview" (1989) *Pharmacol. Ther.* 44:407–443.

Warren et al.; "Increased Accumulation of Drugs in Multidrug–Resistant Cell Induced by Liposomes" (1992) *Cancer Research* 52:3241–3245.

Watkins, Paul B.; "The Role of Cytochromes P–450 in Cyclosporine Metabolism" (1990) *J. Am. Acad. Dermacol.* 23:1301–1309.

Weinberg, David S. et al., "Sublingual absorption of selected opioid analgesics", (1988), *Clin. Pharmacol. Ther.;* Department of Neurology and Department of Pharmacology, Cornell University Medical College, pp. 335–342.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption and Metabolism" (1993) *Pharm. Res.* 10:abstract ppdm8185.

Zamora et al.; "Physical–Chemical Properties Shared by Compounds that Modulate Multidrug Resistance in Human Loukemic Cells" (1988) *Molec. Pharmacol.* 33:454–462.

U.S. Appl. No. 09/286,818, filed Apr. 6, 1999.
U.S. Appl. No. 09/421,905, filed Oct. 20, 1999.
U.S. Appl. No. 09/510,878, filed Feb. 23, 2000.
U.S. Appl. No. 09/535,458, filed Mar. 24, 2000.
U.S. Appl. No. 09/552,290, filed Apr. 19, 2000.
U.S. Appl. No. 09/591,256, filed Jun. 9, 2000.
U.S. Appl. No. 09/592,400, filed Jun. 13, 2000.
U.S. Appl. No. 09/618,808, filed Jul. 18, 2000.
U.S. Appl. No. 09/621,643, filed Jul. 21, 2000.
U.S. Appl. No. 09/631,326, filed Aug. 3, 2000.
U.S. Appl. No. 09/651,514, filed Aug. 30, 2000.
U.S. Appl. No. 09/654,464, filed Sep. 1, 2000.
U.S. Appl. No. 09/653,669, filed Sep. 1, 2000.
U.S. Appl. No. 09/671,552, filed Sep. 27, 2000.

U.S. Appl. No. 09/714,571, filed Nov. 16, 2000.
U.S. Appl. No. 09/747,323, filed Dec. 22, 2000.
U.S. Appl. No. 09/747,300, filed Dec. 22, 2000.
U.S. Appl. No. 09/748,699, filed Dec. 22, 2000.
U.S. Appl. No. 09/749,983, filed Dec. 27, 2000.
U.S. Appl. No. 09/759,561, filed Jan. 11, 2001.
U.S. Appl. No. 09/759,838, filed Jan. 11, 2001.
"Flavor Encapsulation Technologies, Flavor Unit Sweet, Product Management", H&R (undated) (published at least before Nov. 27, 1996), 25 pages.
Dr. Massimo Calanchi and Dr. Sam Ghanta, "Taste–masking of oral formulations", *Eurand International SpA, Pharmaceutical Manufacturing International,* 1996 (5 pages).
The Eurand Group, Brochure (undated) (published at least before Nov. 27, 1996), (16 pages).
Merck Index, 11$^{th}$ Ed., #1635 "Caffeine" (1989), p. 248.
Merck Index, 12$^{th}$ Ed., #2337 "Cimetidine" (1996), p. 383.
Merck Index, 12$^{th}$ Ed., #3264 "Dimethicone" (1996), p. 544.
Merck Index, 12$^{th}$ Ed., #3972 "Famotidine" (1996), p. 667.
Merck Index, 12$^{th}$ Ed., #6758 "Nizatidine" (1996), p. 1143.
Merck Index, 12$^{th}$ Ed., #6977 "Omeprazole" (1996), p. 1174.
Merck Index, 12$^{th}$ Ed., #8272 "Rabeprazole" (1996), p. 1392.
Merck Index, 12$^{th}$ Ed., #8286 "Ranitidine" (1996), p. 1395.
James G. Elliott, "Application of Antioxidant Vitamins in Foods and Beverages" *Food Technology,* (Feb., 1999), pp. 46–48.
C. Curtis Vreeland, "Nutraceuticals Fuel Confectionary Growth" *Candy R&D,* (Mar., 1999), pp. 29, 31–32, 34–35.
Kitty Broihier, R.D., "Foods of Tomorrow, Milking The Nutrition Market", *Food Processing,* (Mar., 1999), pp. 41, 42 and 44.
Kitty Broihier, R.D., "Tea Time For Nutraceuticals, New Black, Green Tea Products Brew Up a Bevy of Health Benefits", *Food Processing,* (Mar., 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), (Mar., 1999).
Product package "Aspergum" distributed by Heritage Consumer Products, LLC (on sale prior to Nov. 27, 1995).
Product package "Chew & Sooth Zinc Dietary Supplement Gum" by Gumtech International, Inc. (undated).
Product Package "Dental Care the Baking Soda Gum" distributed by Church & Dwight Co., Inc. (1998).
Product package "BreathAsure Dental Gum" distributed by Breath Asure, Inc. (1998).
Product package "Trident Advantage with Baking Soda" distributed by Warner–Lambert Co. (1998).
Product package "CHOOZ Antacid/Calcium Supplement with Calcium Carbonate" distributed by Heritage Consumer Products Co.
Heritage Consumer Products Co. article from the Internet "Cosmetics and Toiletries, The Heritage Story", printed Jul. 20, 2000, <http://www.cnewsusa.com/Connecticut/14997.html>, 1 page.
The United States Pharmacopeia The National Formulary— "General Information", dated Jan. 1, 1990 pp 1624–1625 and pp 1696–1697.
Gumtech article from the Internet "Customized Solutions For Customer Brands", printed Oct. 18, 2000, <http://www.gum–tech.com/cus–brands.html>, 3 pages.
Rabeprazole article from the Internet "Rabeprazole: Pharmacokinetics and Safety in the Elderly", printed Sep. 22, 2000, <http://www.mmhc.com/cg/articles/CG9905/Humphries.html>, 2 pages.
Product package for Stay Alert Caffeine Supplement Gum, distributed by Amurol Confections Company (first quarter 1998).

* cited by examiner

NUTRACEUTICALS OR NUTRITIONAL SUPPLEMENTS AND METHOD OF MAKING

REFERENCE TO EARLIER FILED APPLICATIONS

The present application claims the benefit under 35 U.S.C. § 119(e) of the filing date of U.S. Provisional Patent Application No. 60/112,389, filed Dec. 15, 1998. The application is a continuation of PCT Application Ser. No. US99/29792, filed Dec. 14, 1999, which designated the United States. Said PCT application is a continuation-in-part of U.S. patent application Ser. No. 09/389,211, filed Sep. 2, 1999, now abandoned, a continuation-in-part of U.S. patent application Ser. No. 09/286,818, filed Apr. 6, 1999 and a continuation-in-part of U.S. patent application Ser. No. 09/308,972, filed May 27, 1999, now U.S. Pat. No. 6,165,516, which is a nationalization of PCT/US96/18977, filed Nov. 27, 1996. Each of the foregoing applications are hereby incorporated by reference.

BACKGROUND OF THE INVENTION

The present invention relates to methods for producing chewing gum. More particularly, the invention relates to producing chewing gum containing an effective amount of an active medicament. Preferably, the active medicament that is added to the chewing gum has been treated to control its rate of release from chewing gum or the chewing gum formulation has been modified to control the release of medicament for maximum effectiveness.

In recent years, efforts have been devoted to controlling release characteristics of various ingredients in chewing gum. Most notably, attempts have been made to delay the release of sweeteners and flavors in various chewing gum formulations to thereby lengthen the satisfactory chewing time of the gum. Delaying the release of sweeteners and flavors can also avoid an undesirable overpowering burst of sweetness or flavor during the initial chewing period. On the other hand, some ingredients have been treated so as to increase their rate of release in chewing gum.

Besides sweeteners, other ingredients may require a controlled release from chewing gum. In certain embodiments, it is contemplated that the active medicament that is added to the gum is not generally released very readily. An active medicament may be encapsulated in a water soluble matrix such that, during the chewing period, the medicament may be released quickly, resulting in a fast release. This would allow chewing gum to be a carrier for an active medicament with these fast release characteristics.

In some instances, serious taste problems may arise because of the bitter nature of many active medicaments. A prolonged or delayed release of active medicaments would allow for the use of the active medicaments in gum, but the low level of release of such medicaments may keep the level of that agent below the taste threshold of the active medicaments and not give chewing gum a bitter taste quality. In addition, active medicaments may also have other unpleasant tastes that may be overcome by reducing the release rate of active medicaments from a chewing gum.

Another aspect of the present invention contemplates the use of encapsulation techniques. For example, it may be that active medicaments may also be unstable in a chewing gum environment. In such cases, various methods of encapsulation may be needed to improve stability of the active medicament. In other circumstances, active medicaments may not be readily released from the chewing gum matrix and their effect may be considerably reduced. In such a situation, a fast release encapsulation may be needed to release active medicament from the gum matrix.

Other methods contemplated are methods of controlling release of active medicament from gum. These methods would be useful in not releasing the active medicament in the oral cavity during gum chewing, but allowing the active medicament to be ingested during chewing. This will keep the active medicament from becoming effective until after it enters the digestive track.

It is of course known to provide active medicaments to individuals for various purposes. These medicaments can be used to treat diseases and as such are typically referred to as drugs or medicaments. Likewise, the drugs or medicaments can be used for preventive purposes. Still, it is known to provide medicaments to an individual for a variety of non-medical purposes including enhancing performance or maintaining health.

There are a great variety of such medicaments. These medicaments run the gamut from stimulants such as caffeine to drugs such as analgesics, tranquilizers, cardiovascular products, as well as vitamins, minerals, and supplements. Some such medicaments are taken on an "as-needed" basis while other medicaments must be taken at regular intervals by the individual.

Typically, drugs or medicaments are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Oral administration of drugs is by far the most common method of moving drugs towards systemic circulation. When administered orally, drug absorption usually occurs due to the transport of cells across the membranes of the epithelial cells within the gastrointestinal tract. Absorption after oral administration is confounded by numerous factors. These factors include differences down the alimentary cannel in: the luminal pH; surface area per luminal volume; perfusion of tissue, bile, and mucus flow; and the epithelial membranes. See *Merck Manual* at page 2599.

A further issue affecting the absorption or orally administered drugs is the form of the drug. Most orally administered drugs are in the form of tablets or capsules. This is primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that affect the dissolution rate and therefore determine the availability of the drug for absorption. See *Merck Manual* at page 2600.

When a drug rapidly dissolves from a drug product and readily passes across membranes, absorption from most site administration tends to be complete. This is not always the case for drugs given orally. Before reaching the vena cava, the drug must move down the alimentary canal and pass through the gut wall and liver, which are common sites of drug metabolism. Thus, the drug may be metabolized before it can be measured in the general circulation. This cause of a decrease in drug input is called the first pass effect. A large number of drugs show low bioavailability owning to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parenteral administration does provide a method for eliminating a number of the variables that are present with oral administration, parenteral administration is not a preferable route. Typically parenteral administration requires the use of medical personnel and is just not warranted nor practical for the administration of most agents and drugs, e.g., analgesics. Even when required, parenteral administration is not preferred due to patient concerns including comfort, infection, etc., as well as the equipment and costs involved.

There is therefore a need for an improved method of delivering drugs and agents to an individual.

SUMMARY OF THE INVENTION

The present invention provides improved methods for delivering a medicament or active agent to an individual. To this end, chewing gum is provided including a medicament or active agent. The medicament or active agent is present within the chewing gum composition (the water soluble portion and/or insoluble base portion). It has been found that by chewing the gum, the medicament or active agent is released from the chewing gum into saliva. Possibly, saliva coats the oral tissues under the tongue (sublingual) and the sides of the mouth where the drug may partition from the saliva into the oral mucosa. Continuing to chew the chewing gum creates a pressure within the buccal cavity and may force the medicament or active agent or medicament directly into the systemic system of the individual through the oral mucosa contained in the buccal cavity. This greatly enhances the absorption of the drug into the systemic system as well as the bioavailability of the drug within the system.

Improved chewing gum formulations including medicaments and active agents are also provided by the present invention.

To this end, the present invention provides a method of drug delivery comprising the steps of: providing a chewing gum that includes a medicament in the chewing gum composition; chewing the chewing gum to cause the medicament to be released from the chewing gum composition into the buccal cavity of the chewer.

The active medicament may be any agent that is traditionally used as a medicament and lends itself to being administered through the oral cavity. Such active agents may be vitamins, cancer chemotherapeutics; antimycotics; oral contraceptives, nicotine or nicotine replacement agents, minerals, antibacterial agents, anesthetics, antitussives, diuretics, anti-inflammatories, antibiotics, AIDS medication, neurological drugs, antivirals, psychotherapeutic agents, anti-diabetic agents and cardiovascular agents, nutraceuticals and nutritional supplements.

Accordingly, an advantage of the present invention is to provide new methods for delivering medicaments or active agents to an individual.

Still further, an advantage of the present invention is to provide a method of delivering medicaments to an individual that provides for increase absorption and bioavailability as compared to medicaments that are designed to be absorbed in the GI tract.

Further, an advantage of the present invention is to provide a method of administering a medicament or agent to an individual at a lower level than is typically administered orally while still achieving the same effect.

Furthermore, an advantage of the present invention is to provide a method for administering drugs or agents to an individual that heretofore were administered parenterally.

Additionally, an advantage of the present invention is to provide a method of administering drugs that is more palatable than current methods.

Moreover, an advantage of the present invention is to provide an improved method for drug delivery.

The present invention also provides a method of producing chewing gum with physically modified active medicaments to control their release. Such active medicaments are added to a gum coating to deliver the active medicaments systemically without unpleasant tastes. The present invention also relates to the chewing gum so produced. Physically modified active medicaments may be added to sucrose-type gum formulations and sucrose-type coatings. The formulation may be a low or high moisture formulation containing low or high amounts of moisture containing syrup. Physically modified active medicaments may also be used in low or non-sugar gum formulations and coatings that use sorbitol, mannitol, other polyols or carbohydrates. Non-sugar formulations may include low or high moisture sugar-free chewing gums.

Active medicaments described herein may be combined or co-dried with bulk sweeteners typically used in chewing gum before the active medicaments are physically modified. Such bulk sweeteners are sucrose, dextrose, fructose and maltodextrins, as well as sugar alcohols such as sorbitol, mannitol, xylitol, maltitol, lactitol, hydrogenated isomaltulose and hydrogenated starch hydrolyzates.

The modified release rate noted above may be a fast release or a delayed release. The modified release of active medicaments may be obtained by encapsulation, partial encapsulation or partial coating, entrapment or absorption with high or low water soluble materials or water insoluble materials. The procedures for modifying the active medicaments include spray drying, spray chilling, fluid bed coating, coacervation, extrusion and other agglomerating and standard encapsulating techniques. The active medicaments also may be absorbed onto an inert or water-insoluble material. Active medicaments may be modified in a multiple step process comprising any of the processes, or a combination of the processes noted. Prior to encapsulation, active medicaments may also be combined with bulk sweeteners including sucrose, dextrose, fructose, maltodextrin or other bulk sweeteners, as well as sugar alcohols such as sorbitol, mannitol, xylitol, maltitol, lactitol, hydrogenated isomaltulose and hydrogenated starch hydrolyzates.

Prior to encapsulation, active medicaments may be combined with high-intensity sweeteners, including but not limited to thaumatin, aspartame, alitame, acesulfame K, saccharin acid and its salts, glycyrrhizin, cyclamate and its salts, stevioside and dihydrochalcones. Co-encapsulation of active medicaments along with a high-intensity sweetener may reduce the poor taste qualities of active medicaments and control the sweetener release with active medicaments. This can improve the quality of the gum product and increase consumer acceptability.

DETAILED DESCRIPTION OF THE PREFERRED EMBODIMENTS

The present invention provides improved methods for delivering medicaments and other active agents to an individual as well as improved formulations including such medicaments and agents. Pursuant to the present invention, a physically modified medicament or active is contained in a chewing gum formulation. In contrast to some prior such formulations, the medicament or agent is contained directly in the chewing gum composition.

Accordingly, as the chewing gum is chewed, the physically modified active is released into the saliva. During continual chewing, the medicament or active in the saliva may be then forced due to the pressure created by the chewing gum through the oral mucosa in the buccal cavity. The oral mucosa favors drug absorption. In contrast to a typically oral ingested drug, wherein the solution is in contact too briefly for absorption to be appreciable through the oral mucosa, it is believed that during the chewing, the physically modified active agent and/or medicament remains in the buccal cavity and may be forced or partitioned through the oral mucosa. An increase in the absorption of the drug may be achieved as well as an increase in the bioavailability of the drug as compared to typical oral administration. The drug or active agent may be absorbed much quicker than if it was swallowed as in a typical oral administration. Indeed, the absorption approaches that of a parental administration and bioavailability may be also much greater than oral administration.

It is also possible that less physically modified medicament or active agent can be placed in the chewing gum than is typically orally administered to an individual to achieve an effect and the same bioequivalence can be achieved. In some instances, for certain drugs and agents, the administration of the medicament or agent using chewing gum through the buccal activity may provide an increase in therapeutic effect even as compared to parenteral administration.

For example, caffeine is commonly used as a stimulant to alleviate the effects of sleep deprivation. It is almost completely metabolized in the liver and therefore classified as a low clearance, flow independent drug. This means its rate of inactivation is unaffected by delivery to the liver and can only be modified by a change in the hepatic enzyme activity.

Data set forth in detail in U.S. patent application Ser. No. 09/386,818 herein incorporated by reference, suggests that the absorption rate constant (Ka) is significantly increased when caffeine is administrated through chewing gum versus a pill. This means that the caffeine is moving into the systemic circulation at a significantly faster rate. A similar change in the onset of dynamic response has also been noted, e.g., alertness and performance.

When caffeine is added to stick chewing gum at a level of about 0.2% to about 5%, caffeine imparts an intense bitterness to the chewing gum that lasts throughout the chewing period. The higher the level used, the stronger the bitterness. At about 0.2%, which is about 5 mg per 2.7 gram stick, the bitterness is below the threshold limit and is not readily discernible. Taste limits in stick chewing gum are generally about 0.4% (10 mg) to about 4% (100 mg) of caffeine in a stick of gum. The 60–80 mg level of caffeine is about the level of caffeine found in a conventional cup of coffee. The target level of caffeine in stick gum is about 40 mg per stick, with a range of about 25–60 mg, so that a five stick package of gum would contain about 200 mg of caffeine, or the equivalent of caffeine in two strong cups of coffee. However, at this level caffeine bitterness overwhelms the flavor initially and lasts throughout the chewing period.

For coated pellet gum, piece weight is generally about 1.5 grams per piece. However, one coated piece of gum is about equal to ½ piece of stick gum. Two pellets are equivalent to a stick of gum, and together weigh about 3 grams. The above-noted target level of 40 mg per stick is equivalent to 20 mg per coated piece, or a range of about 12 to 30 mg caffeine per piece. This is about 0.8% to about 2% caffeine in a piece of coated gum, or a target level of 1.3%.

Caffeine is a slightly water soluble substance and, therefore, has a moderately slow release from stick chewing gum. Caffeine is 2.1% soluble in water at room temperature, 15% soluble in water at 80° C. and 40% soluble in boiling water. This gives caffeine a moderately slow release as shown below:

| Chewing Time | % Caffeine Release |
| --- | --- |
| 0 min | — |
| 5 min | 56 |
| 10 min | 73 |
| 20 min | 88 |
| 40 min | 97 |

Generally, highly water soluble ingredients such as sugars in stick gum are about 80–90% released after only five minutes of chewing. For caffeine, only about 50% is released, while the other 50% remains in the gum after five minutes of chewing. After 20 minutes almost 90% of caffeine is released.

Even if caffeine is dissolved in hot water and mixed in the stick gum, when the gum is cooled or kept at room temperature, caffeine may return to its normal crystalline state and release at a rate similar to that shown above.

When a physically modified active such as caffeine is added to a gum stick, the active agent will have an increased water solubility, and release quickly into the mouth from the gum. Depending on the active agent, which may generally be non-water soluble, physically modifying the active agent by various forms at encapsulation will increase the release of the active agent from chewing gum. Most water soluble active agents can be modified by encapsulation to give a more uniform release from chewing gum. Depending on the active agent and the type of encapsulation used, the level released from the gum into the mouth can be adjusted for maximum effectiveness.

Other agents or medicaments may be included in the present invention. By the terms "active agent" the present invention refers to a compound that has a desired therapeutic or physiological effect once ingested and/or metabolized. The therapeutic effect may be one which decreases the growth of a xenobiotic or other gut flora or fauna, alters the activity of an enzyme, provides the physical relief from a malady (e.g., diminishes pain, acid reflux or other discomfort), has an effect on the brain chemistry of molecules that determine mood and behavior. Of course these are just examples of what is intended by therapeutic effect. Those of skill in the art will readily recognize that a particular agent has or is associated with a given therapeutic effect.

The active agent may be any agent that is traditionally used as a medicament and lends itself to being administered through the oral cavity. Such active agents may be vitamins, cancer chemotherapeutics; antimycotics; oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents and cardiovascular agents, bioengineered pharmaceuticals, nutraceuticals and nutritional supplements. Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K.

Examples of cancer chemotherapeutics agents include but are not limited to cisplatin (CDDP), procarbazine, mechlorethamine, cyclophosphamide, camptothecin, ifosfamide, melphalan, chlorambucil, bisulfan, nitrosurea, dactinomycin: daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, P-lactamase inhibitors; meziocillin, piperacillin, aztreonam, norfloxacin, trimethoprim, ceftazidime, dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscamet, ganciclovir, zidovudine, dideoxycytosine, dideoxyinosine, stavudine, famciclovir, didanosine, zalcitabine, rifimantadine, and cytokines.

Antacids include cimetidine, ranitidine, nizatidine, famotidine, omeprazole, bismuth antacids, metronidazole antacids, tetracylcine antacids, clarthromycin antacids, hydroxides of aluminum, magnesium, sodium bicarbonates, calcium bicarbonate and other carbonates, silicates, and phosphates.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include agents such as dextromethorphan hydrobromide, levopropoxyphene napsylate, noscapine, carbetapentane, caramiphen, chlophediaonl, pseudoephedrine hydrochloride pseudoephedrine sulfate, phenylephidrine, diphenhydramine, glaucine, pholcodine, and benzonatate.

Anesthetics include etomidate, ketamine, propofol, and benodiazapines (e.g., chlordiazepoxide, diazepame, clorezepate, halazepam, flurazepam, quazepam, estazolam, triazolam, alprazolm, midazolam, temazepam, oxazepam, lorazepam), benzocaine, dyclonine, bupivacaine, etidocaine, lidocaine, mepivacaine, promoxine, prilocaine, procaine, proparcaine, ropivacaine, tetracaine. Other useful agents may include amobartital, aprobarbital, butabarbital, butalbital mephobarbital, methohexital, pentobarbital, phenobarbital, secobarbital, thiopental, paral, chloralhydrate, ethchlorvynol, clutethimide, methprylon, ethinamate, and meprobarnate.

Analgesics include opioids and other medicaments such as morphine, mepidine, dentanyl, sufentranil, alfentanil, aspirin, acetaminophen, ibuprofen, indomethacine, naproxen, atrin, isocome, midrin, axotal, firinal, phrenilin, ergot, and ergot derivatives (wigraine, cafergot, ergostat, ergomar, dihydroergotamine), imitrex, and ketoprofen.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprion olactone, canrenone, and potassium canrenoate.

Anti-inflammatories include but are not limited to salicylic acid derivatives (e.g. aspirin), indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone).

Psychotherapeutic agents include thorazine, serentil, mellaril, millazinetindal, permitil, prolixin, trilafon, stelazine, suprazine, taractan, navan, clozaril, haldol, halperon, loxitane, moban, orap, risperdal, alprazolam, chordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, wellbutrin, serzone, desyrel, nardil, parnate, eldepryl.

Cardiovascular agents include but are not limited to nitroglycerin, isosorbide dinitrate, sodium nitroprisside, captopril, enalaprill, enalaprilat, quinapril, lisinopril, ramipril, losartan, amrinone, linnone, vesnerinone, hydralazine, nicorandil, prozasin, doxazosin, bunazosin, tamutosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine, or a sexual dysfunction agent like sildenafil citrate (Viagra).

It is envisioned that depending on the active agent or medicament, the resultant chewing gum can be used to treat inter alia: coughs, colds, motion sickness; allergies; fevers; pain; inflammation; sore throats; cold sores; migraines; sinus problems; diarrhea; diabetes, gastritis; depression; anxiety, hypertension; angina and other maladies and symptoms. Also these gums may be useful in ameliorating cravings in substance abuse withdrawal or for appetite suppression. Specific active agents or medicaments include by way of example and limitation: caffeine, aspirin, acetaminophen; ibuprofen; ketoprofen; cimetidine, ranitidine, famotidine, dramamine, omeprazole, dyclonine hydrochloride, chlorpheniramine maleate, pseudoephedrine hydrochloride, dextromethorphan hydrobromide; benzocaine, sodium naproxen, and nicotine.

Compositions that may be formulated into a suitable chewing gum formulation are described in, for examples, U.S. Pat. No. 5,858,423; U.S. Pat. No. 5,858,413; U.S. Pat. No. 5,858,412 and U.S. Pat. No. 5,858,383. Additionally, Goodman and Gilman's "The Pharmaceutical Basis of Therapeutics" (Eds. Hardman et al., Publ. McGraw Hill, NY) provides comprehensive guidance of useful drugs and their mechanisms of action. Medicated chewing gums have been particularly effective in the delivery of agents such as nicotine as described in for example, U.S. Pat. No. 5,866,179; and U.S. Pat. No. 5,889,028. U.S. Pat. No. 5,846,557 describes general chewing gum compositions containing cough suppressing agents. These patents are incorporated herein by reference as providing a teaching of the incorporation of medicinal agents into oral chewable formulations. It should be understood that the present chewing gum formulation(s) are not limited to the agents listed herein above, indeed any medicinal or other active agent that lends itself to ingestion may be formulated into the chewing gum formulations of the present invention.

Nutraceuticals and nutritional supplements may also be added to chewing gums as active agents. Among these are herbs and botanicals that include, but are not limited to capsicum, chamomile, cat's claw, echinacea, garlic, ginger, ginko, various ginseng, green tea, golden seal, kava kava, nettle, passion flower, saw palmetto, St. John's wort, and valerian. Also included are mineral supplements such as calcium, copper, iodine, iron, magnesium, manganese, molybdenum, phosphorous, selenium and zinc. Other nutraceuticals that also can be added to chewing gum as active agents are benzoin, fructo-oligosaccharides, glucosamine, grapeseed extract, guarana, inulin, phosphotidylserine, phytosterols, phytochemicals, isoflavones, lecithin, lycopene, oligofructose, polyphenol and psyllium as well as weight loss agents such as chromium picolinate and phenylpropanolamine.

Preferably, the agents or medicaments are contained in the chewing gum formulation at levels of approximately 50 micrograms to 500 milligrams. The specific levels will depend on the active ingredient. For example, if chromium picolinate is the active ingredient in an embodiment, it would be present at a level of 50 micrograms per serving (2.8 grams stick of gum); aspirin would be preset at a level of 325 milligrams per 2.8/gram serving (stick).

The level of medicament or agent in the chewing gum formulation is selected so as to create, when the gum is chewed, a sufficiently high concentration of the medicament or agent in the saliva.

For example, when the agent is a stimulant such as nicotine or caffeine, the level of the stimulant in the chewing gum should be such that it creates a saliva content of stimulant of approximately 15 to 440 ppm when the chewing gum is chewed for 2 minutes. At this level, a sufficient amount of stimulant will be delivered to the chewer to create the effects set forth in the application. It a medicament is used such as a medicinal agent (e.g., analgesics), sufficient medicinal agent should be present in the chewing gum to create a salvia content of approximately 1700 to approximately 4400 ppm after the chewing gum has been chewed for 2 minutes. For botanical agents (e.g., chamomile, kava, kola, nut, ginseng, and Echinacea), the agent should be present in a sufficient amount to create a saliva content of approximately 85 to 1100 ppm when the chewing gum is chewed for 2 minutes. For a metabolizer, for example, chromium picolinate and hydroxi-chitic acid, the agents should be present in an amount to create a saliva content of approximately 0.5 to about 900 ppm when chewed for at least two minutes. If the agent is a vitamin or mineral (e.g., phosphatidy serine, vitamin C, and zinc), the agent should be present in the amount to create a saliva content of the vitamin or mineral of approximately 10 to about 250 ppm when chewed for 2 minutes.

Pursuant to the present invention, depending on the agent or medicament, the dosing regiment will change. For example, if the medicament is an analgesic, the chewing gum would be taken on an as needed basis. Of course, similar to the oral administration of an analgesic, there would be restrictions on the number of pieces of chewing gum chewed, for example, not more often than one stick every four hours and not more often than four to five times a day. If the agent is a stimulant such as caffeine to be used to enhance performance than the chewing gum would be chewed, in a preferred embodiment ten minutes or less before the performance.

The medicament or agent can be contained in a variety of different chewing gum compositions. Referring now to the chewing gum, pursuant to the present invention, the chewing gum including the medicament or agent may be based on a variety of different chewing gums that are known. For example, the chewing gums can be low or high moisture, sugar or sugarless, wax containing or wax free, low calorie (via high base or low calorie bulking agents), and/or may contain dental agents.

Physical modifications of the active agent encapsulation with a highly water soluble substrate will increase its release in stick chewing gum as well as from the gum coating by increasing the solubility or dissolution rate. However, the active agent may also be encapsulated or entrapped to give a delayed release from stick chewing gum and from a gum coating. Any standard technique which gives partial or full encapsulation of the active agent can be used. These techniques include, but are not limited to, spray drying, spray chilling, fluid-bed coating and coacervation. These encapsulation techniques may be used individually in a single step process or in any combination in a multiple step process.

Active agents may be encapsulated with sweeteners, more specifically high-intensity sweeteners such as thaumatin, dihydrochalcones, acesulfame K, aspartame, N-substituted APM derivatives such as neotame, sucralose, alitame, saccharin and cyclamates. These can also have the effect of reducing unpleasant tastes such as bitterness. Additional bitterness inhibitors or taste maskers can also be combined with active agents and sweeteners to give a reduced unpleasant taste such as bitterness with delayed release active agent(s).

The encapsulation techniques described herein are standard coating techniques and generally give varying degrees of coating from partial to full coating, depending on the coating composition used in the process. Generally, compositions that have high organic solubility, good film-forming properties and low water solubility give better delayed release of active agents such as caffeine, while compositions that have high water solubility give better fast release. Such low water-solubility compositions include acrylic polymers and copolymers, carboxyvinyl polymer, polyamides, polystyrene, polyvinyl acetate, polyvinyl acetate phthalate, polyvinylpyrrolidone and waxes. Although all of these materials are possible for encapsulation of active agents such as caffeine, only food-grade materials should be considered. Two standard food-grade coating materials that are good film formers but not water soluble are shellac and Zein. Others which are more water soluble, but good film formers, are materials like agar, alginates, a wide range of cellulose derivatives like ethyl cellulose, methyl cellulose, sodium hydroxymethyl cellulose, and hydroxypropylmethyl cellulose, dextrin, gelatin, and modified starches. These ingredients, which are generally approved for food use, may give a fast release when used as an encapsulant. Other encapsulants like acacia or maltodextrin can also encapsulate active agent(s) and give a fast release rate in gum.

The amount of coating or encapsulating material on the active agent also may control the length of time for its release from chewing gum. Generally, the higher the level of coating and the lower the amount of active agent, the slower the release during mastication with low water soluble compositions. The release rate is generally not instantaneous, but gradual over an extended period of time for stick gum. Delayed release allows the active agent to be masked in the mouth before being ingested, thus reducing bitterness or other unpleasant tastes. To obtain the delayed release, the encapsulant should be a minimum of about 20% of the coated active. Preferably, the encapsulant should be a minimum of about 30% of the coated active, and most preferably should be a minimum of about 40% of the coated active. Generally, water soluble encapsulating agents will increase the release rate of water insoluble active agents.

Another method of giving a modified release of active agent and the other agents described herein is agglomeration with agglomerating agent which partially coats the active agents. This method includes the step of mixing active agents and an agglomerating agent with a small amount of water or solvent. The mixture is prepared in such a way as to have individual wet particles in contact with each other so that a partial coating can be applied. After the water or other solvent is removed, the mixture is ground and used as a powdered active agent.

Materials that can be used as the agglomerating agent are the same as those used in encapsulation mentioned previously. Some of the better agglomerating agents for delayed release are the organic polymers like acrylic polymers and copolymers, polyvinyl acetate, polyvinylpyrrolidone, waxes, shellac and Zein. Other agglomerating agents are not as effective in giving a delayed release as are the polymers, waxes, shellac and Zein, but can be used to give some delayed release. Other agglomerating agents include, but are not limited to, agar, alginates, a wide range of water soluble cellulose derivatives like ethyl cellulose, methyl cellulose, sodium hydroxymethyl cellulose, hydroxypropylmethyl cellulose, dextrin, gelatin, modified starches, and vegetable gums like guar gum, locust bean gum and carrageenan. Even though the agglomerated active agent is only partially coated, when the quantity of coating is increased compared to the quantity of the active agent, the release can also be modified. The level of coating used in the agglomerated product is a minimum of about 5%. Preferably, the coating level is a minimum of about 15% and more preferably about 20%. Depending on the agglomerating agent, a higher or lower amount of agent may be needed to give the desired release of the active agent. Generally, water soluble agglomerants will increase the rate of release of water insoluble active agents.

Active agents may be coated in a two-step process or a multiple step process. Active agents may be encapsulated with any of the materials as described previously and then the encapsulated caffeine or other active agents can be agglomerated as previously described to obtain an encapsulated/agglomerated active agent product that could be used in chewing gum to give a delayed release of the active agent.

In another embodiment of this invention, active agent may be absorbed onto another component which is porous and becomes entrapped in the matrix of the porous component. Common materials used for absorbing active agents include, but are not limited to, silicas, silicates, pharmasorb clay, sponge-like beads or microbeads, amorphous carbonates and hydroxides, including aluminum and calcium lakes, all of which result in a delayed release of caffeine or other active agent.

Depending on the type of absorbent materials and how it is prepared, the amount of active agent that can be loaded onto the absorbent will vary. Generally materials like polymers or sponge-like beads or microbeads, amorphous sugars and alditols and amorphous carbonates and hydroxides absorb about 10% to about 40% of the weight of the absorbent. Other materials like silicas and pharmasorb clays may be able to absorb about 20% to about 80% of the weight of the absorbent. Generally, water soluble absorbants will increase the release rate of water insoluble active agents.

The general procedure for absorbing active agent onto the absorbent is as follows. An absorbent like fumed silica powder can be mixed in a powder blender and a solution of active agent can be sprayed onto the powder as mixing continues. The aqueous solution can be about 1 to 2% solids, and higher solid levels to 15–30% may be used if temperatures up to 90° C. are used. Generally water is the solvent, but other solvents like alcohol could also be used if approved. As the powder mixes, the liquid is sprayed onto the powder. Spraying is stopped before the mix becomes damp. The still free-flowing powder is removed from the mixer and dried to remove the water or other solvent, and is then ground to a specific particle size.

After the active agent is absorbed or fixed onto an absorbent, the fixative/active agent can be coated by encapsulation. Either full or partial encapsulation may be used, depending on the coating composition used in the process. Full encapsulation may be obtained by coating with a polymer as in spray drying, spray chilling, fluid-bed coating, coapervation, or any other standard technique. A partial encapsulation or coating can be obtained by agglomeration of the fixative/active agent mixture using any of the materials discussed above.

Another form of encapsulation is by entrapment of an ingredient by fiber extrusion or fiber spinning into a polymer. Polymers that can be used for extrusion are PVAC, hydroxypropyl cellulose, polyethylene and other types of plastic polymers. A process of encapsulation by fiber extrusion is disclosed in U.S. Pat. No. 4,978,537, which is hereby incorporated by reference. The water insoluble polymer may be preblended with caffeine or other active agents prior to fiber extrusion, or may be added after the polymer is melted. As the extrudate is extruded, it results in small fibers that are cooled and ground. This type of encapsulation/entrapment generally gives a very long, delayed release of an active ingredient.

The four primary methods to obtain a treated active agent are: (1) encapsulation by spray drying, fluid-bed coating, spray chilling and coacervation to give full or partial encapsulation, (2) agglomeration to give partial encapsulation, (3) fixation or absorption which also gives partial encapsulation, and (4) entrapment into an extruded compound. These four methods, combined in any usable manner which physically modifies active agents dissolvability or modifies the release of active agents, are included in this invention.

Medicament actives may be combined in a chewing gum. In a stick gum, two, three, or more actives may be added to a single piece. One active could be encapsulated for fast release, another active for moderate release, and another active for slow release. In addition, a single medicament active could be encapsulated and entrapped to release at various times as the gum is being chewed. This type of gum formulation could be effective for time release medication.

Medicament actives may also be combined in a coated chewing gum product. A single active may be added to a gum coating for fast release and also added to the gum center with or without encapsulation for slow release. If the active has an affinity for the gum base it may naturally give a slow release without encapsulation. If the active is fast release it would have to be encapsulated or entrapped for the desired time release.

A combination of medicament actives may be used in the gum coating and in the gum center for various reasons. In some cases, medicaments may be reactive to one another and should be kept from coming in contact with each other. In other cases, combinations of medicaments may be used for various symptoms where multiple medicaments may be effective. For example, a decongestant such as pseudoephedrine may be added to a gum coating and an antihistamine such as chlorpheniramine may be added to a gum center to treat cold/allergy symptoms. For sore throat, an oral anesthetic like dyclonine hydrochloride may be used in the gum coating and an antibacterial agent like cetyl pyridinium chloride may be added to a gum center. Additionally, any other materials like dextromethorphan hydrobromide for cough relief or an analgesic like ketoprofen may be added to either a gum coating and a gum center for cold symptoms. Other combinations of medicament active agents for other types of ailments are also within the scope of this invention.

In many instances a medicament may have a bitter taste. If the medicament were added to a coating at a very low level, it would still have the effect of fast release initially. In this case, the active agent may be added to the gum coating at a very low level beneath its taste threshold. Additional active agent that is encapsulated and entrapped may then be added to the gum center for slow release. This bitter active agent can then be kept below its taste threshold level and release slowly as the gum is being chewed, but the active agent would continue to be released to give its effective dosage.

In many instances, active medicaments may have a low quality off-taste or bitterness, especially if added to a chewing gum coating. In most cases, this off taste may be masked with high intensity sweeteners, but in other instances, a bitterness inhibitor may be needed to reduce a bitter taste of a medicament.

There are a wide variety of bitterness inhibitors that can be used in food products as well as with active agents. Some of the preferred bitterness inhibitors are the sodium salts which are discussed in the article *Suppression of Bitterness by Sodium: Variations Among Bitter Taste Stimuli*, by R. A. S. Breslin and G. K. Beceuchenp from Monell Chemical Senses Center, Philadelphia, Pa. Sodium salts discussed are sodium acetate and sodium gluconate. Other sodium salts that may also be effective are sodium glycinate, sodium ascorbate and sodium glycerolphosphate. Among these, the most preferred is sodium gluconate and sodium glycinate since they have a low salty taste and are most effective to reduce bitterness of most active medicaments.

Most of the sodium salts are very water soluble and are readily released from chewing gum to function as bitterness inhibitors. In most instances, the sodium salts which release readily from chewing gum may be modified by encapsulation to give an even faster release from chewing gum. However, in some instances the sodium salts would be encapsulated or entrapped to give a delayed release from gum. Generally, the bitterness inhibitor should release with the active medicament for maximum effectiveness.

In addition to physically modifying the active medicament for fast or delayed release, medicaments may be dissolved in solvents, flavors, or other transdermal vehicles used as absorption enhancing agents and added to gum or to a gum coating. The absorption enhancing agents may also be added to the gum or gum coating separately from the active ingredient. Their presence may help volatilize medicaments or allow increased buccaVlingual absorption of the active agent through the nasal mucosal or the lungs. These solvents, flavors, or transdermal vehicles may transport medicaments faster through the oral mucosa.

Faster absorption may be affected by increasing flavor levels as well as the addition of other flavor components, such as menthol and menthol derivatives, limonene, carvone, isomenthol, eucalyptol, menthone, pynene, camphor and camphor derivatives, as well as monoterpene natural products, monoterpene derivatives, and sesquaterpenes, including caryophyllene and copaene. Other vehicles that may be used to increase transdermal absorption are: ethanol, polyethylene glycol, 2-pyrrolidones, myristic acid, Brij-35 (surfactant), p-phenyl phenol, nitrobenzene, stearyl alcohol, cetyl alcohol, croton oil, liquid paraffin, dimethyl sulfoxide (DMSO), non-ionic surfactants, liposomes, lecithin fractions, and long chain amphipathic molecules (molecules with polar or non-ionized groups on one end and non-polar groups at the other end).

In addition, some polysaccharides such as cellulose gums, natural gums like guar gum, gum arabic, and others may be mixed with active medicaments or mixed in the gum formulation with the medicament. This may allow the medicaments to stick to the surface of the oral mucosa during chewing and increase oral absorption. Bioadhesives may act in a similar manner to achieve increased absorption of the active medicament.

In some instances the gum formulation may have an effect on release rate of the medicament. Water miscible medicaments may be released more slowly when using a highly hydrophillic gum base and more quickly from a lipophillic gum base. On the other hand, oil miscible medicaments may release more quickly when using a highly hydrophillic gum base and more slowly from a lipophillic gum base. Also medicaments may release more quickly by using high HLB solubilizers in the gum formulation. Medicaments may also be emulsified together with water soluble bulking agents to increase release of the medicaments.

Other gum formula modifications may also affect the release rate of medicaments. Texture modifiers to soften base may give faster release where hard bases may give slower release. Addition of alkaline materials such as sodium bicarbonate or sodium hydroxide may make the saliva slightly alkaline, which may increase buccaVlingual absorption of the medicament into the bloodstream. Use of a buffer in the gum formula may affect release rate or absorption or shelf life of certain medicaments or supplements. Gum base made with talc may offer unique release and shelf life improvements. Other additives, such as astringents may give the sensation of dry mouth, which may improve medicament absorption. Also, some types of hot, spicy flavors such as ginger or hot pepper may give the impression of high activity of the medicament.

Medicaments may be added to chewing gum via special carriers which may affect the release rate and its absorption. Some carriers that may be used are activated charcoal, molecular sieves, corn starch granules, microsponges, or liposomes. The medicament may be sugar or polyol candy coated, or entrapped in cyclodextrin for fast release to dissolve quickly in the mouth during chewing.

Release of the medicament from gum may also be effected by particle size of the coated medicament. Small particles release more quickly whereas large particles more slowly. Fast release can also be accomplished by dissolving medicament in a liquid and used in a liquid center gum. Some medicaments may be advantageous to use in both slow and fast release. Quick release may give good oral absorption, then slow release may result by swallowing the cud. This may be particularly effective if a biodegradable gum base is used. On the other hand, some medicaments may have an advantage with a slow initial release, but increases later. This can reduce side effects of the medicament and improve adaptation to the medicament. Slow release may also be accomplished by attaching a medicament to a polymer used in the chewing gum.

Release of a medicament or active agent may also be effected by the shape and size of the chewing gum product. Flat stick pieces of gum with large surface area may release actives faster into saliva from gum when chewed, whereas round or cube pieces may release medicaments and actives more slowly. Gum formulations, especially those that are anhydrous or have no gum softening agents may be ground to a powder. This powder may be dusted onto the surface of another gum formulation or coated onto a ball or pillow shape gum product. This powder may also be tabletted in a tablet press to give a unique form to be chewed for release of its active agent. Other forms of gum to be used are rolled sticks, or soft squeezable gum from a tube.

Active medicaments can also be added to chewing gum formulations that are made into tablets. Tableting of chewing gum is disclosed in U.K. Patent Publication No. 1,489,832; U.S. Pat. No. 4,753,805; EP Patent Publication No. 0 221 850; and Italy Patent Publication No. 1,273,487. These patents disclose active agents added to chewing gum which is then tableted. As an embodiment of this invention, active agents may be encapsulated or entrapped and added to a chewing gum formulation which is then tableted. In addition, a formed chewing gum tablet may also be used as a core for a coated chewing gum pellet that is coated with a sugar, polyol or film. The chewing gum core may contain one active agent or multiple active medicaments and the coating may contain one or more active medicaments. This form will yield unique chewing gum products.

The previously described encapsulated, agglomerated or absorbed active agent may readily be added to a chewing gum composition. The remainder of the chewing gum ingredients are well known to those of skill in the art and are not intended to be limiting to the present invention. That is, the treated particles of active agent can be added to conventional chewing gum formulations in a conventional manner. Treated active agent may be added to a sugar chewing gum or a sugarless chewing gum.

In general, a chewing gum composition typically comprises a water-soluble bulk portion, a water-insoluble chewable grams base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

In a particular embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate—vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, N-substituted APM derivatives such as neotame, salts of acesulfame, altitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

If the medicament or active is water soluble in the chewing gum, it preferably will include a base/emulsifier system which leads to the desired concentration of the medicament in the saliva (more hydrophilic balance). If the medicament or active is water insoluble, the chewing gum preferably includes a base/emulsifier system which leads to the desired concentration of the medicament in the saliva (more lipophilic balance).

In manufacturing the chewing gum including the active agent or ingredient, the active agent or medicament is added, preferably, early on in the mix. The smaller the amount of active ingredient used, the more necessary it becomes to preblend that particular ingredient to assume uniform distribution throughout the batch of gum. Whether a preblend is used or not, the active agent or medicament should be added within the first five minutes of mixing. For faster release, the active agent may be added late in the process.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

Chewing gum base and chewing gum product have been manufactured conventionally using separate mixers, different mixing technologies and, often, at different factories. One reason for this is that the optimum conditions for manufacturing gum base, and for manufacturing chewing gum from gum base and other ingredients such as sweeteners and flavors, are so different that it has been impractical to integrate both tasks. Chewing gum base manufacture, on the one hand, involves the dispersive (often high shear) mixing of difficult-to-blend ingredients such as elastomer, filler, elastomer plasticizer, base softeners/emulsifiers and sometimes wax, and typically requires long mixing times. Chewing gum product manufacture, on the other hand, involves combining the gum base with more delicate ingredients such as product softeners, bulk sweeteners, high Intensity sweeteners and flavoring agents using distributive (generally lower shear) mixing, for shorter periods.

In order to improve the efficiency of gum base and gum product manufacture, there has been a trend toward the continuous manufacture of gum bases and products. U.S. Pat. No. 3,995,064, issued to Ehrgott et al., discloses the continuous manufacture of gum base using a sequence of mixers or a single variable mixer. U.S. Pat. No. 4,459,311, issued to DeTora et al., also discloses the continuous manufacture of gum base using a sequence of mixers. Other continuous gum base manufacturing processes are disclosed in European Publication No. 0,273,809 (General Foods France) and in French Publication No. 2,635,441 (General Foods France).

U.S. Pat. No. 5,045,325, issued to Lesko et al., and U.S. Pat. No. 4,555,407, issued to Kramer et al., disclose processes for the continuous production of chewing gum products. In each case, however, the gum base is initially prepared separately and is simply added into the process. U.S. Pat. No. 4,968,511, issued to D'Amelia et al., discloses a chewing gum product containing certain vinyl polymers which can be produced in a direct one-step process not requiring separate manufacture of gum base.

Active medicaments may also be added to chewing gum products made by a continuous process. U.S. Pat. Nos. 5,543,160 and 5,800,847 disclose a continuous process using a single extruder to make the gum base and the gum product. U.S. Pat. Nos. 5,397,580 and 5,523,097 disclose a continuous process using two or more extruders for base and chewing gum mixing. U.S. Pat. Nos. 5,419,919 and 5,571,543 disclose a continuous process using a paddle type mixer which has low pressure and high residence time for adequate mixing.

Active medicaments, whether encapsulated, entrapped or not, can be added at any time during the continuous mixing process. Generally, actives would probably be added in the gum mixing sections. Specific advantages to adding active medicaments to a continuous process of manufacturing gum are that more thorough mixing is accomplished in this type of process with lower amount of residence time of the active agent at high temperatures during processing. The enclosed system used in continuous processing can result in more thorough mixing, better reproducibility of the amount of active within the gum matrix, and less loss in the amount of the active medicament.

Another method of treating the medicament or active agent is to physically isolate the active agent from other chewing gum ingredients to effect its release rate and stability. The active agent may be added to the liquid inside a liquid center gum product. The center fill of gum product may comprise one or more carbohydrate syrups, glycerin, thickeners, flavors, acidulants, colors, sugars and sugar alcohols in conventional amounts. The ingredients are combined in a conventional manner. The total amount of active agent may be dissolved in the center-fill liquid. This method of using active agent in chewing gum may give a more controlled release rate, and may reduce or eliminate any possible reaction with gum base, flavor components, or other components, yielding improved shelf stability. A liquid-center gum may also be coated with a sugar, polyol or film to yield a unique chewing gum product.

Another method of isolating medicaments or active agents from other chewing gum ingredients is to add active agents to the dusting compound of a chewing gum. A rolling or dusting compound serves to reduce sticking to machinery as it is wrapped, and sticking to its wrapper after it is wrapped and being stored. The rolling compound comprises active agents in combination with mannitol, sorbitol, sucrose, starch, calcium carbonate, talc, other orally acceptable substances or a combination thereof. The rolling compound constitutes from about 0.25% to about 10.0% or about 1% to about 3% of weight of the chewing gum composition. This method of using active agents in the chewing gum can allow a lower usage level, can give a more controlled release rate, and can reduce or eliminate any possible reaction with the gum base, flavor components, or other components, yielding improved self stability.

Another method of isolating medicament or active agents is to use it in the coating/panning of a pellet chewing gum. Pellet or ball gum is prepared as conventional chewing gum but formed into pellets that are pillow shaped, or into balls. The pellets/balls can be then sugar coated or panned by conventional panning techniques to make a unique coated pellet gum. The active agent may be soluble in flavor or can be blended with other powders often used in some types of conventional panning procedures. Active agents are isolated from other gum ingredients which modifies its release rate from chewing gum. Levels of actives may be about 10 ppm to 5% by weight of chewing gum coating. The weight of the coating may be about 20% to about 50% of the weight of the finished product, but may be as much as 75% of the total gum product.

Conventional panning procedures generally coat with sucrose, but recent advances in panning have allowed use of other carbohydrate materials to be used in place of sucrose. Some of these components include, but are not limited to, dextrose, maltose, palatinose, xylitol, lactitol, hydrogenated isomaltulose, erythritol maltitol, and other new alditols or combinations thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetables gums like alginates, locust bean gum, guar gum, and gum tragacanth, insoluble carbonates like calcium carbonate or magnesium carbonate and talc. Antitack agents may also be added as panning modifiers, which allow the use of a variety of carbohydrates and sugar alcohols to be used in the development of new panned or coated gum products. Flavors may also be added with the sugar or sugarless coating and with the active to yield unique product characteristics.

Another type of pan coating could also isolate the active agent from the chewing gum ingredients. This technique is referred to as a film coating and is more common for pharmaceuticals than in chewing gum, but procedures are similar. A film like shellac, zein, or cellulose type material is applied onto a pellet-type product forming a thin film on the surface of the product. The film is applied by mixing the polymer, plasticizer and a solvent (pigments are optional) and spraying the mixture onto the pellet surface. This is done in conventional type panning equipment, or in more advanced side-vented coating pans. Since most active agents may be alcohol soluble, they may be readily added with this type of film. When a solvent like an alcohol is used, extra precautions are needed to prevent fires and explosions, and specialized equipment must be used.

Some film polymers can use water as the solvent in film coating. Recent advances in polymer research and in film coating technology eliminates the problem associated with the use of solvents in coating. These advances make it possible to apply aqueous films to a pellet or chewing gum product. Some active agents can be added to this aqueous film or even the alcohol solvent film, in which an active agent is highly soluble. This film may also contain a flavor along with a polymer and plasticizer. The active agent can also be dissolved in the aqueous solvent and coated on the surface with the aqueous film. This will give a unique sweetness release to a film-coated product.

After a coating film with an active medicament is applied to a chewing gum product, a hard shell sugar or polyol coating may then be applied over the film coated product. In some instances a soft shell sugar or polyol coating may also be used over the film coated product. The level of film coating applied to a pellet gum may be generally about 0.5% to about 3% of the gum product. The level of overcoating of the hard or soft shell may be about 20% to about 60%. When the active agent is added with the film coating and not with the sugar/polyol coating, better control of the amount of active agent in the product may be obtained. In addition, the sugar/polyol overcoating may give an improved stability to the active agent in the product.

As noted above, the coating may contain ingredients such as flavoring agents, as well as artificial sweeteners and dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent.

Artificial sweeteners contemplated for use in the coating include but are not limited to synthetic substances, saccharin, thaumatin, alitame, saccharin salts, aspartame, N-substituted APM derivatives such as neotame, sucralose and acesulfame-K. The artificial sweetener may be added to the coating syrup in an amount such that the coating will contain from about 0.01% to about 0.5%, and preferably from about 0.1% to about 0.3% artificial sweetener.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1.0%, and preferably from about 0.3% to about 0.6% of the agent.

Coloring agents are preferably added directly to the syrup in the dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha (another type of acacia), alginate, cellulosics, vegetable gums and the like.

The coating is initially present as a liquid syrup which contains from about 30% to about 80% or 85% of the coating ingredients previously described herein, and from about 15% or 20% to about 70% of a solvent such as water. In general, the coating process is carried out in a rotating pan. Sugar or sugarless gum center tablets to be coated are placed into the rotating pan to form a moving mass.

The material or syrup which will eventually form the coating is applied or distributed over the gum center tablets. Flavoring agents may be added before, during and after applying the syrup to the gum centers. Once the coating has dried to form a hard surface, additional syrup additions can be made to produce a plurality of coatings or multiple layers of hard coating.

In a hard coating panning procedure, syrup is added to the gum center tablets at a temperature range of from about 100° F. to about 240° F. Preferably, the syrup temperature is from about 130° F. to about 200° F. throughout the process in order to prevent the polyol or sugar in the syrup from crystallizing. The syrup may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup. Any number of coats may be applied to the gum center tablet. Preferably, no more than about 75–100 coats are applied to the gum center tablets. The present invention contemplates applying an amount of syrup sufficient to yield a coated comestible containing about 10% to about 65% coating. Where higher dosage of an active agent is needed, the final product may be higher than 65% coating.

Those skilled in the art will recognize that in order to obtain a plurality of coated layers, a plurality of premeasured aliquots of coating syrup may be applied to the gum center tablets. It is contemplated, however, that the volume of aliquots of syrup applied to the gum center tablets may vary throughout the coating procedure.

Once a coating of syrup is applied to the gum center tablets, the present invention contemplates drying the wet syrup in an inert medium. A preferred drying medium comprises air. Preferably, forced drying air contacts the wet syrup coating in a temperature range of from about 70° to about 115° F. More preferably, the drying air is in the temperature range of from about 800 to about 100° F. The invention also contemplates that the drying air possess a relative humidity of less than about 15 percent. Preferably, the relative humidity of the drying air is less than about 8 percent.

The drying air may be passed over and admixed with the syrup coated gum centers in any way commonly known in the art. Preferably, the drying air is blown over and around or through the bed of the syrup coated gum centers at a flow rate, for large scale operations, of about 2800 cubic feet per minute. If lower quantities of material are being processed, or if smaller equipment is used, lower flow rates would be used.

For many years, flavors have been added to a sugar coating of pellet gum to enhance the overall flavor of gum. These flavors include spearmint flavor, peppermint flavor, wintergreen flavor, and fruit flavors. These flavors are generally preblended with the coating syrup just prior to applying it to the core or added together to the core in one or more coating applications in a revolving pan containing the cores. Generally, the coating syrup is very hot, about 130° to 200° F., and the flavor may volatilize if preblended with the coating syrup too early.

The concentrated coating syrup is applied to the gum cores as a hot liquid, the sugar or polyol allowed to crystallize, and the coating then dried with warm, dry air. This is repeated in about 30 to 80 applications to obtain a hard shell coated product having an increased weight gain of about 40% to 75%. A flavor is applied with one, two, three or even four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these type of fruit flavors are not used in coatings.

In an embodiment of this invention, an active agent is preblended with a gum arabic solution to become a paste and then applied to the cores. To reduce stickiness, the preblend may be mixed with a small amount of coating syrup before being applied. Forced air drying is then continued as the gum arabic binds the active agent to the cores. Then additional coatings are applied to cover the active agent and imbed the treated active agent in the coatings.

Gum Formulation Examples

The following examples of the invention and comparative examples are provided by way of explanation and illustration.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas for pellet centers are generally adjusted to a higher level of gum base to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 40% gum base with a corresponding decrease in the other ingredients except flavor. Even higher levels of base may be used if an active is added to a pellet coating. Generally flavors increase with the level of gum base as the base tends to bind flavors into the gum and more flavor is needed to give a good flavorful product. However flavors can also be added to the coating to give increased flavor impact and more flavor perception.

A wide range of changes and modifications to the embodiments of the invention described above will be apparent to persons skilled in the art. For example, while the invention is described with respect to hard-coated chewing gum, it will be appreciated that the process is applicable to coating other food products, such as candies, in which a coating with dyclonine hydrochloride would have utility.

EXAMPLES

The following examples of the invention and comparative examples are provided by way of explanation and illustration.

The formulas listed in Table 1 comprise various sugar-type formulas in which active medicament can be added to gum after it is dissolved in water or mixed with various aqueous solvents. Dyclonine hydrochloride is an active medicament used as an oral anesthetic for sore throat. These formulas give a 3 gram stick with 3 mg of dyclonine hydrochloride.

TABLE 1

(WEIGHT PERCENT)

| | EX. 1 | EX. 2 | EX. 3 | EX. 4 | EX. 5 | EX. 6 | EX. 7 | EX. 8 |
|---|---|---|---|---|---|---|---|---|
| SUGAR | 62.5 | 64.6 | 63.6 | 65.0 | 65.0 | 63.0 | 61.6 | 47.0 |
| BASE | 19.2 | 19.2 | 19.2 | 19.2 | 19.2 | 19.2 | 19.2 | 19.2 |
| CORN SYRUP | 15.9 | 12.9 | 12.9 | 12.9 | 12.9 | 15.9 | 0.0 | 2.9 |
| PEPPERMINT FLAVOR | 0.9 | 0.9 | 0.9 | 0.9 | 0.9 | 0.0 | 0.9 | 0.9 |
| GLYCERIN | 1.4 | 1.4 | 1.4 | 0.0 | 0.0 | 0.9 | 1.4 | 0.0 |

TABLE 1-continued (WEIGHT PERCENT)

| | EX. 1 | EX. 2 | EX. 3 | EX. 4 | EX. 5 | EX. 6 | EX. 7 | EX. 8 |
|---|---|---|---|---|---|---|---|---|
| LIQUID/ACTIVE BLEND | 0.1 | 1.0 | 2.0 | 2.0 | 2.0 | 1.0 | 16.9 | 30.0 |

Example 1

Dyclonine hydrochloride powder can be added directly to the gum.

Example 2

A 1 gram quantity of dyclonine hydrochloride can be dissolved in 9 grams of water giving a 10% solution and added to gum.

Example 3

A 1 gram quantity of dyclonine hydrochloride can be dissolved in 9 grams of water and mixed with 10 grams of glycerin and added to the gum.

Example 4

A 1 gram quantity of dyclonine hydrochloride is mixed with 19 grams of glycerin giving a 5% solution and added to gum.

Example 5

A 1 gram quantity of dyclonine hydrochloride is mixed with 19 grams of propylene glycol giving a 5% solution and added to gum.

Example 6

A 1 gram quantity of dyclonine hydrochloride is dissolved in 9 grams of ethanol, which is then mixed with 90 grams of peppermint flavor and added to gum.

Example 7

A 1 gram quantity of dyclonine hydrochloride is dissolved in 168 grams of corn syrup and added to chewing gum.

Example 8

To a 200 gram quantity of corn syrup is added 100 grams of glycerin. To this mixture is added 1 gram of dyclonine hydrochloride and blended. This mixture is then added to gum.

In the next examples of sugar formulations, dyclonine hydrochloride can be dissolved in water and emulsifiers can be added to the aqueous solution. Example solutions can be prepared by dissolving 10 grams of dyclonine hydrochloride in 75 grams of water and adding 15 grams of emulsifiers of various hydrophilic-lipophilic balance (HLB) values to the solution. The mixtures can then be used in the following formulas. Example 9 uses a mixture of dyclonine hydrochloride and water with no emulsifier. The HLB value of the emulsifiers used in Examples 10–14 are listed in Table 2.

TABLE 2

| | (WEIGHT PERCENT) | | | | | |
|---|---|---|---|---|---|---|
| | EX. 9 | EX. 10 | EX. 11 | EX. 12 | EX. 13 | EX. 14 |
| SUGAR | 54.7 | 54.7 | 54.7 | 54.7 | 54.7 | 54.7 |
| BASE | 19.2 | 19.2 | 19.2 | 19.2 | 19.2 | 19.2 |
| CORN SYRUP | 12.9 | 12.9 | 12.9 | 12.9 | 12.9 | 12.9 |
| GLYCERIN | 1.4 | 1.4. | 1.4 | 1.4 | 1.4 | 1.4 |
| DEXTROSE MONO-HYDRATE | 9.9 | 9.9 | 9.9 | 9.9 | 9.9 | 9.9 |
| PEPP. FLAVOR | 0.9 | 0.9 | 0.9 | 0.9 | 0.9 | 0.9 |
| ACTIVE AGENT EMULSIFIER/ WATER MIXTURE | 1.0 | 1.0 | 1.0 | 1.0 | 1.0 | 1.0 |
| | None | HLB = 2 | HLB = 4 | HLB = 6 | HLB = 9 | HLB = 12 |

Examples 15–20

The same as the formulations made in Examples 9–14, respectively, except that the flavor can be mixed together with the aqueous dyclonine hydrochloride solution and emulsified before adding the mixture to the gum batch.

The following Tables 3 through 10 are examples of gum formulations that demonstrate formula variations in which dyclonine hydrochloride may be used. The active agent may be added with or without encapsulation, or may be treated for fast release.

Examples 21–24 in Table 3 demonstrates the use of dyclonine hydrochloride in low-moisture sugar formulations showing less than 2% theoretical moisture:

TABLE 3

| | (WEIGHT PERCENT) | | | |
|---|---|---|---|---|
| | EX. 21 | EX. 22 | EX. 23 | EX. 24 |
| SUGAR | 58.8 | 58.6 | 58.8 | 54.6 |
| GUM BASE | 19.2 | 19.2 | 19.2 | 19.2 |
| CORN SYRUP[a] | 6.0 | 6.0 | — | — |
| DEXTROSE MONOHY-DRATE | 10.0 | 10.0 | 10.0 | 10.0 |
| LACTOSE | 0.0 | 0.0 | 0.0 | 5.0 |
| GLYCERIN[b] | 5.0 | 5.0 | 11.0 | 10.0 |
| FLAVOR | 0.9 | 0.9 | 0.9 | 0.9 |
| ACTIVE DYCLONINE HYDRO-CHLORIDE | 0.1 | 0.3 | 0.1 | 0.3 |

[a]Corn syrup is evaporated to 85% solids, 15% moisture
[b]Glycerin and syrup may be blended and co-evaporated Examples 25–28 in Table 4 demonstrate the use of dyclonine hydrochloride in medium-moisture sugar formulations having about 2% to about 5% moisture.

Examples 29–32 in Table 5 demonstrate the use of dyclonine hydrochloride in high-moisture sugar formulations having more than about 5% moisture.

TABLE 4

| | (WEIGHT PERCENT) | | | |
|---|---|---|---|---|
| | EX. 25 | EX. 26 | EX. 27 | EX. 28 |
| SUGAR | 53.4 | 53.2 | 53.4 | 49.7 |
| GUM BASE | 19.2 | 19.2 | 19.2 | 19.2 |
| CORN SYRUP[a] | 15.0 | 15.0 | 13.0 | 12.5 |

TABLE 4-continued

| | (WEIGHT PERCENT) | | | |
|---|---|---|---|---|
| | EX. 25 | EX. 26 | EX. 27 | EX. 28 |
| DEXTROSE MONOHY-DRATE | 10.0 | 10.0 | 10.0 | 10.0 |
| GLYCERIN[b] | 1.4 | 1.4 | 3.4 | 7.4 |
| FLAVOR | 0.9 | 0.9 | 0.9 | 0.9 |
| ACTIVE DYCLONINE HYDRO-CHLORIDE | 0.1 | 0.3 | 0.1 | 0.3 |

[a]Corn syrup is evaporated to 85% solids, 15% moisture
[b]Glycerin and syrup may be blended and co-evaporated

TABLE 5

| | (WEIGHT PERCENT) | | | |
|---|---|---|---|---|
| | EX. 29 | EX. 30 | EX. 31 | EX. 32 |
| SUGAR | 50.9 | 50.7 | 49.9 | 49.7 |
| GUM BASE | 24.0 | 24.0 | 24 0 | 24.0 |
| CORN SYRUP | 24.0 | 24.0 | 24.0 | 24.6 |
| GLYCERIN | 0.0 | 0.0 | 1.0 | 0.4 |
| FLAVOR | 1.0 | 1.0 | 1.0 | 1.0 |
| ACTIVE DYCLONINE HYDRO-CHLORIDE | 0.1 | 0.3 | 0.1 | 0.3 |

Examples 33–36 in Table 6 and Examples 37–44 in Tables 7 and 8 demonstrate the use of dyclonine hydrochloride in low- and high-moisture gums that are sugar-free. Low-moisture gums have less than about 2% moisture, and high-moisture gums have greater than 2% moisture.

TABLE 6

| | (WEIGHT PERCENT) | | | |
|---|---|---|---|---|
| | EX. 33 | EX. 34 | EX. 35 | EX. 36 |
| BASE | 25.5 | 25.5 | 25.5 | 25.5 |
| SORBITOL | 50.9 | 50.7 | 48.9 | 45.7 |
| MANNITOL | 12.0 | 12.0 | 12.0 | 12.0 |
| GLYCERIN | 10.0 | 10.0 | 12.0 | 15.0 |
| FLAVOR | 1.5 | 1.5 | 1.5 | 1.5 |
| ACTIVE DYCLONINE HYDRO-CHLORIDE | 0.1 | 0.3 | 0.1 | 0.3 |

TABLE 7

| | (WEIGHT PERCENT) | | | |
|---|---|---|---|---|
| | EX. 37 | EX. 38 | EX. 39 | EX. 40 |
| BASE | 25.5 | 25.5 | 25.5 | 25.5 |
| SORBITOL | 50.9 | 50.7 | 40.9 | 40.7 |
| LIQUID SORBITOL* | 10.0 | 10.0 | 20.0 | 20.0 |
| MANNITOL | 10.0 | 10.0 | 10.0 | 10.0 |
| GLYCERIN | 2.0 | 2.0 | 2.0 | 2.0 |
| FLAVOR | 1.5 | 1.5 | 1.5 | 1.5 |
| ACTIVE DYCLONINE HYDROCHLORIDE | 0.1 | 0.3 | 0.1 | 0.3 |

*Sorbitol liquid contains 70% sorbitol, 30% water

TABLE 8

| | (WEIGHT PERCENT) | | | |
|---|---|---|---|---|
| | EX. 41 | EX. 42 | EX. 43 | EX. 44 |
| BASE | 25.5 | 25.5 | 25.5 | 25.5 |
| SORBITOL | 50.9 | 48.7 | 44.9 | 42.7 |
| HSH SYRUP* | 10.0 | 10.0 | 10.0 | 10.0 |
| MANNITOL | 8.0 | 8.0 | 8.0 | 8.0 |
| GLYCERIN** | 4.0 | 6.0 | 10.0 | 12.0 |
| FLAVOR | 1.5 | 1.5 | 1.5 | 1.5 |
| ACTIVE DYCLONINE HYDROCHLORIDE | 0.1 | 0.3 | 0.1 | 0.3 |

*Hydrogenated starch hydrolyzate syrup
**Glycerin and HSH syrup may be blended or co-evaporated Table 9 shows sugar chewing formulations that can be made with various types of sugars.

TABLE 9

| | (WEIGHT PERCENT) | | | | | | | | | | | |
|---|---|---|---|---|---|---|---|---|---|---|---|---|
| | EX. 45 | EX. 46 | EX. 47 | EX. 48 | EX. 49 | EX. 50 | EX. 51 | EX. 52 | EX. 53 | EX. 54 | EX. 55 | EX. 56 |
| GUM BASE | 19.2 | 19.2 | 19.2 | 19.2 | 19.2 | 19.2 | 19.2 | 19.2 | 19.2 | 19.2 | 19.2 | 19.2 |
| SUCROSE | 49.4 | 48.2 | 44.4 | 39.2 | 34.4 | 42.2 | 34.4 | 43.2 | 34.4 | 43.2 | 42.4 | 45.2 |
| GLYCERIN | 1.4 | 2.4 | 1.4 | 6.4 | 1.4 | 3.4 | 1.4 | 2.4 | 1.4 | 2.4 | 1.4 | 3.4 |
| CORN SYRUP | 14.0 | 14.0 | 14.0 | 14.0 | 14.0 | 14.0 | 14.0 | 14.0 | 14.0 | 14.0 | 11.0 | 11.0 |
| DEXTROSE | 5.0 | 5.0 | — | — | 10.0 | 5.0 | 10.0 | 5.0 | 10.0 | 5.0 | 10.0 | 5.0 |
| LACTOSE | 5.0 | 5.0 | 10.0 | 10.0 | — | — | — | — | — | — | — | — |
| FRUCTOSE | 5.0 | 5.0 | 10.0 | 10.0 | 10.0 | 5.0 | 10.0 | 5.0 | 10.0 | 5.0 | 5.0 | 5.0 |
| INVERT SUGAR | — | — | — | — | 10.0 | 10.0 | 10.0 | 10.0 | — | — | 5.0 | 5.0 |
| MALTOSE | — | — | — | — | — | — | — | — | 10.0 | 10.0 | — | — |
| CORN SYRUP SOLIDS | — | — | — | — | — | — | — | — | — | — | 5.0 | 5.0 |
| PEPPERMINT FLAVOR | 0.9 | 0.9 | 0.9 | 0.9 | 0.9 | 0.9 | 0.9 | 0.9 | 0.9 | 0.9 | 0.9 | 0.9 |
| ACTIVE DYCLONINE HYDROCHLORIDE | 0.1 | 0.3 | 0.1 | 0.3 | 0.1 | 0.3 | 0.1 | 0.3 | 0.1 | 0.3 | 0.1 | 0.3 |

Table 10 shows chewing gum formulations that are free of sugar. These formulations can use a wide variety of other non-sugar alditols.

TABLE 10

| | (WEIGHT PERCENT) | | | | | | | | | | | |
|---|---|---|---|---|---|---|---|---|---|---|---|---|
| | EX. 57 | EX. 58 | EX. 59 | EX. 60 | EX. 61 | EX. 62 | EX. 63 | EX. 64 | EX. 65 | EX. 66 | EX. 67 | EX. 68 |
| GUM BASE | 25.5 | 25.5 | 25.5 | 25.5 | 25.5 | 25.5 | 25.5 | 25.5 | 25.5 | 25.5 | 25.5 | 25.5 |
| GLYCERIN | 8.0 | 8.0 | 8.0 | 8.0 | 8.0 | 2.0 | 8.0 | 8.0 | 8.0 | 2.0 | 8.0 | 2.0 |
| SORBITOL | 47.9 | 37.7 | 37.9 | 32.7 | 31.9 | 29.7 | 41.9 | 36.7 | 31.9 | 40.7 | 29.9 | 29.7 |
| MANNITOL | — | 10.0 | 10.0 | 10.0 | 10.0 | 6.0 | 8.0 | 8.0 | 8.0 | — | — | — |
| SORBITOL LIQUID | 17.0 | 17.0 | — | — | — | — | 5.0 | — | — | — | — | — |
| LYCASIN | — | — | 17.0 | 12.0 | 8.0 | 20.0 | — | 5.0 | 5.0 | 5.0 | 10.0 | 20.0 |
| MALTITOL | — | — | — | 10.0 | — | — | — | 5.0 | — | — | — | — |
| XYLITOL | — | — | — | — | 15.0 | 15.0 | — | — | — | 15.0 | 15.0 | 11.0 |
| LACTITOL | — | — | — | — | — | — | 10.0 | 10.0 | 10.0 | — | — | — |
| PALATINIT | — | — | — | — | — | — | — | — | 10.0 | 10.0 | 10.0 | 10.0 |
| FLAVOR | 1.5 | 1.5 | 1.5 | 1.5 | 1.5 | 1.5 | 1.5 | 1.5 | 1.5 | 1.5 | 1.5 | 1.5 |
| ACTIVE DYCLONINE HYDROCHLORIDE | 0.1 | 0.3 | 0.1 | 0.3 | 0.1 | 0.3 | 0.1 | 0.3 | 0.1 | 0.3 | 0.1 | 0.3 |

High-intensity sweeteners (HIS) such as aspartame, acesulfame K, or the salts of acesulfame, cyclamate and its salts, saccharin and its salts, alitame, neotame, sucralose, thaumatin, monellin, dihydrochalcone, stevioside, glycyrrhizin, and combinations thereof may be used in any of the Examples listed in Tables 3, 4, 5, 6, 7, 8, 9 and 10. Since dyclonine hydrochloride may reduce sweetness, HIS may be used in sugar gum, and some of the alditols in sugar-free gum are less sweet than sugar so higher levels of HIS may be needed to obtain the proper level of sweetness.

High-intensity sweeteners may also be modified to control their release in those chewing gum formulations. This can be controlled by various methods of encapsulation, agglomeration, absorption, or a combination of methods to obtain either a fast or slow release of the sweetener. Sweetener combinations, some of which may be synergistic, may also be included in the gum formulations.

Example 69—A 50% shellac, 50% active dyclonine hydrochloride powder mixture is obtained by spray drying an appropriate ratio alcohoVshellac/dyclonine hydrochloride mixture at 10% solids.

Example 70—A 70% Zein, 30% active dyclonine hydrochloride powder mixture is obtained by spray drying an alcohol/Zein/dyclonine hydrochloride mixture at 10% solids.

Example 71—A 40% shellac, 60% active dyclonine hydrochloride powder mixture is obtained by fluid-bed coating dyclonine hydrochloride with an alcohol/shellac solution at 20% solids.

Example 72—A 40% Zein, 60% active dyclonine hydrochloride powder mixture is obtained by fluid-bed coating dyclonine hydrochloride with an alcohol/Zein solution of 20% solids.

Example 73—A 70% wax, 30% active dyclonine hydrochloride powder mixture is obtained by spray chilling a mixture of molten wax and dyclonine hydrochloride.

Example 74—A 70% Zein, 30% active dyclonine hydrochloride powder mixture is obtained by spray drying an aqueous mixture of dyclonine hydrochloride and Zein dispersed in an aqueous, high-pH (pH of 11.6–12.0) media at 10% solids.

Examples 69–74 would all give nearly complete encapsulation and would delay the release of dyclonine hydrochloride when used in the sugarless gum formulation. The higher levels of coating would give a longer delayed release of sweetener than the lower levels of coating.

Other polymers that are more water soluble would have less of an effect of delaying the release of the dyclonine hydrochloride if used in the coating.

Example 75—A 30% hydroxpropylmethyl cellulose (HPMC), 70% dyclonine hydrochloride powder mixture is obtained by fluid-bed coating dyclonine hydrochloride with an aqueous solution of HPMC at 10% solids.

Example 76—A 50% maltodextrin, 50% active dyclonine hydrochloride powder mixture is obtained by spray drying an aqueous mixture of dyclonine hydrochloride and maltodextrin at 20% solids.

Example 77—A 40% gum arabic, 60% active dyclonine hydrochloride powder mixture is obtained by fluid-bed coating dyclonine hydrochloride with an aqueous solution of gum arabic at 20% solids.

The coated dyclonine hydrochloride from Examples 75–77, when used in a chewing gum formula, would give a fast release of active agents.

Dyclonine hydrochloride could also be used in gum as an agglomerated active agent to give delayed sweetness release. Agglomerated active agent can be prepared as in the following examples:

Example 78—A 15% hydroxypropylmethyl cellulose (HPMC), 85% active dyclonine hydrochloride powder mixture is prepared by agglomerating dyclonine hydrochloride and HPMC blended together, with water being added, and the resulting product being dried and ground.

Example 79—A 15% gelatin, 85% active dyclonine hydrochloride powder mixture is made by agglomerating dyclonine hydrochloride and gelatin blended together, with water being added, and the resulting product being dried and ground.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 11. Gum center formulas may or may not contain dyclonine hydrochloride.

TABLE 11

(WEIGHT PERCENT)

| | EX. 80 | EX. 81 | EX. 82 | EX. 83 | EX. 84 | EX. 85 |
|---|---|---|---|---|---|---|
| SUGAR | 52.0 | 48.7 | 47.55 | 44.0 | 40.7 | 38.55 |
| GUM BASE | 26.0 | 30.0 | 35.00 | 26.0 | 30.0 | 35.00 |
| CORN SYRUP | 20.0 | 19.0 | 15.00 | 18.0 | 17.0 | 14.00 |
| GLYCERIN | 1.0 | 1.0 | 1.00 | 1.0 | 1.0 | 1.00 |
| PEPPERMINT FLAVOR | 1.0 | 1.0 | 1.00 | 1.0 | 1.0 | 1.00 |
| DEXTROSE MONO-HYDRATE | — | — | — | 10.0 | 10.0 | 10.00 |
| DYCLONINE HYDRO-CHLORIDE | — | 0.3 | 0.45 | — | 0.3 | 0.45 |

Formulations with or without active dyclonine hydrochloride can also be made similar to those found in Tables 3–8 for low, medium, and high moisture formulas. Higher levels of base may be used with a corresponding decrease in other ingredients. Also, other sugars and polyols may be used in the gum center as found in Tables 9–10. Dyclonine hydrochloride may be added to a gum center only, or to a gum coating with none in the center, or to both center and coating. Coated gum pieces are about 1.5 grams, so to obtain 3 mg of dyclonine hydrochloride total piece must contain 0.2%.

Dyclonine hydrochloride can then be used in the coating formula on the various pellet gum formulations. The following Table 12 shows some sugar and dextrose type formulas:

TABLE 12

(DRY WEIGHT PERCENT)

| | EX. 86 | EX. 87 | EX. 88 | EX. 89 | EX. 90 | EX. 91 |
|---|---|---|---|---|---|---|
| SUGAR | 97.1 | 95.2 | 93.5 | 96.9 | 94.9 | 93.0 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| DYCLONINE HYDROCHLORIDE | — | 0.2 | 0.6[a] | — | 0.2 | 0.6[a] |

| | EX. 92 | EX. 93 | EX. 94 | EX. 95 |
|---|---|---|---|---|
| DEXTROSE MONOHYDRATE | 97.6 | 95.2 | 97.0 | 93.9 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| DYCLONINE HYDROCHLORIDE | — | 0.2 | 0.2 | 0.6[a] |

| | EX. 96 | EX. 97 | EX. 98 | EX. 99 | EX. 100 | EX. 101 |
|---|---|---|---|---|---|---|
| SUGAR | 77.5 | 81.2 | — | — | 86.9 | — |
| DEXTROSE MONOHYDRATE | — | — | 77.5 | 86.1 | — | 86.5 |
| POWDER SUGAR | 20.0 | 15.0 | — | — | — | — |
| POWDER DEXTROSE | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |

TABLE 12-continued (DRY WEIGHT PERCENT)

| | | | | | | |
|---|---|---|---|---|---|---|
| DYCLONINE HYDROCHLORIDE | — | 0.2 | — | 0.2 | 0.6[a] | 0.6[a] |

[a]All of the active agent is in the coating, which comprises 33% of the product.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. Table 12 gives these types of formulas.

In Examples 96–99, gum arabic is blended in the sugar syrup. In Examples 100 and 101, gum arabic powder is dry charged after a gum arabic solution is applied in the first stages of coating, then this is followed by a hard shell coating of sugar solution or dextrose solution.

The above formulations are made by making a syrup by dissolving the sugar and gum arabic in solution at about 75% solids at boiling, and suspending titanium dioxide or calcium carbonate in this syrup. Some of the dextrose may be added as a dry charge which may also contain the active agent. Dyclonine hydrochloride may be dissolved in water, not mixed with hot syrup, but added between coatings, or it may be added to the hot syrup and used in the early stages of coating or used throughout the coating process. Flavor is not mixed with the hot syrup, but added at low levels with one or more coats. Dyclonine hydrochloride may be dissolved in flavor and added to the coating. After the final coats are applied and dried, wax is applied to give a smooth polish.

Dyclonine hydrochloride may also be used in coating of sugarless gum centers. Like sugar gum centers, the base formulation can be increased in proportion to the amount of coating applied to the center. Formulations with and without dyclonine hydrochloride similar to those found in Tables 6, 7 or 8 for low and high moisture gum can be used to make gum centers. Generally, the base level may be increased to 30–46% with the other ingredients proportionally reduced. Some typical gum formulas are in Table 13.

TABLE 13

(WEIGHT PERCENT)

| | EX. 102 | EX. 103 | EX. 104[c] | EX. 105 | EX. 106 | EX. 107 | EX. 108[c] |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 45.0 | 45.9 | 40.3 | 44.5 | 41.4 | 26.1 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| ACTIVE DYCLONINE HYDROCHLORIDE[b] | — | 0.3 | 0.4 | — | 0.3 | 0.3 | 0.4 |

[a]Lycasin brand hydrogenated starch hydrolyzate used instead of sorbitol liquid
[b]This material may be dissolved in water, glycerin, sorbitol liquid, or HSH.
[c]These formulas require 50% of the product to be a coating with no active agent, to give a final product with 0.2% active agent.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, lactitol and hydrogenated isomaltulose may also be used in the gum center formulations at various levels similar to those shown in Table 10. The texture may be adjusted by varying glycerin or sorbitol liquid. Sweetness of the center formulation can also be adjusted by varying the level of high intensity sweetener.

Dyclonine hydrochloride may be used in sugarless coatings with xylitol, sorbitol, maltitol, lactitol, hydrogenated isomaltulose and erythritol. The following table gives formulas for a xylitol coating:

TABLE 14

(DRY WEIGHT PERCENT)

|  | EX. 109 | EX. 110 | EX. 111 | EX. 112 | EX. 113 | EX. 114 |
|---|---|---|---|---|---|---|
| XYLITOL | 94.8 | 92.2 | 90.1 | 90.1 | 89.7 | 88.2 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| DYCLONINE HYDROCHLORIDE | — | 0.2 | 0.6$^a$ | — | 0.2 | 0.6$^a$ |

*Lake color dispersed in xylitol solution
**Calcium carbonate used in place of titanium dioxide
$^a$All of the active agent is in the gum coating, which comprises 33% of the gum product.

The above formulas are used to coat pellets by applying a xylitol/gum arabic solution in multiple coats and air drying. Color or whitener is also mixed in the solution. Dyclonine hydrochloride may be dissolved in water and added between coating applications or mixed with the hot syrup and used in the early stages of coating or used throughout the coating process. After pellets have been coated and dried, talc and wax are added to give a polish.

For examples 115–120, erythritol may be substituted for xylitol in Table 14. In some cases more gum arabic may be needed to give good binding.

For coating formulas based on sorbitol, maltitol, lactitol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 15

(DRY WEIGHT PERCENT)

|  | EX. 121 | EX. 122 | EX. 123 | EX. 124 | EX. 125 | EX. 126 |
|---|---|---|---|---|---|---|
| MALTITOL | 98.8 | 94.7 | 91.5 | 86.8 | 75.9 | 68.9 |
| MALTITOL | — | — | — | 10.0 | 20.0 | 25.0 |

TABLE 15-continued (DRY WEIGHT PERCENT)

|  | EX. 121 | EX. 122 | EX. 123 | EX. 124 | EX. 125 | EX. 126 |
|---|---|---|---|---|---|---|
| POWDER |  |  |  |  |  |  |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| DYCLONINE HYDROCHLORIDE | — | 0.2 | 0.6$^a$ | — | 0.2 | 0.6$^a$ |

$^a$All of the active agent is in the coating, which comprises 33% of the product.

Maltitol powder is used to dry charge in the early stages of coating. Maltitol, gum arabic, and whitener are blended into a syrup and applied to pellets. Dyclonine hydrochloride may be applied in a similar manner as in the previous xylitol coating or may be preblended with the dry charge material. After all coating is applied and dried, talc and wax are added to give a polish.

In a similar manner, coatings with sorbitol, lactitol, and hydrogenated isomaltulose may be made in the coating formulas in Table 15 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like dyclonine hydrochloride, gum talha, gum arabic or other moisture absorbing materials. Also, powdered sweeteners or flavors could be added with the dry charge, along with the active medicament.

Some polyols such as sorbitol, maltitol, lactitol, erythritol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

The formulas listed in Table 16 comprise various sugar-type formulas in which chlorpheniramine maleate can be added to gum after it is dissolved in water or mixed with various aqueous solvents. Chlorpheniramine maleate is an active medicament used as an antihistamine. These formulas give a 3 gram stick with 4 mg of chlorpheniramine maleate.

TABLE 16

(WEIGHT PERCENT)

|  | EX. 127 | EX. 128 | EX. 129 | EX. 130 | EX. 131 | EX. 132 | EX. 133 | EX. 134 |
|---|---|---|---|---|---|---|---|---|
| SUGAR | 62.47 | 64.3 | 63.0 | 64.4 | 64.4 | 62.7 | 61.6 | 47.0 |
| BASE | 19.2 | 19.2 | 19.2 | 19.2 | 19.2 | 19.2 | 19.2 | 19.2 |
| CORN SYRUP | 15.9 | 12.9 | 12.9 | 12.9 | 12.9 | 15.9 | 0.0 | 2.9 |
| PEPPERMINT FLAVOR | 0.9 | 0.9 | 0.9 | 0.9 | 0.0 | 0.0 | 0.9 | 0.9 |
| GLYCERIN | 1.4 | 1.4 | 1.4 | 0.0 | 2.2 | 0.9 | 1.4 | 0.0 |
| LIQUID/ ACTIVE BLEND | 0.13 | 1.3 | 2.6 | 2.6 | 1.3 | 1.3 | 16.9 | 30.0 |

Example 127

Chlorpheniramine maleate powder can be added directly to the gum.

Example 128

A 1 gram quantity of chlorpheniramine maleate can be dissolved in 9 grams of water giving a 10% solution and added to gum.

Example 129

A 1 gram quantity of chlorpheniramine maleate can be dissolved in 9 grams of water and mixed with 10 grams of glycerin and added to the gum.

Example 130

A 1 gram quantity of chlorpheniramine maleate is mixed with 19 grams of glycerin giving a 5% solution and added to gum.

Example 131

A 1 gram quantity of chlorpheniramine maleate is mixed with 9 grams of peppermint flavor giving a 10% solution and added to gum.

Example 132

A 1 gram quantity of chlorpheniramine maleate is dissolved in 9 grams of ethanol, which is then mixed with 90 grams of peppermint flavor and added to gum.

Example 133

A 1.3 gram quantity of chlorpheniramine maleate is dissolved in 168 grams of corn syrup and added to chewing gum.

Example 134

To a 200 gram quantity of corn syrup is added 100 grams of glycerin.

To this mixture is added 1.3 gram of chlorpheniramine maleate and blended. This mixture is then added to gum.

In the next examples of sugar formulations, chlorpheniramine maleate can be dissolved in water and emulsifiers can be added to the aqueous solution. Example solutions can be prepared by dissolving 13 grams of chlorpheniramine maleate in 72 grams of water and adding 15 grams of emulsifiers of various hydrophilic-lipophilic balance (HLB) values to the solution. The mixtures can then be used in the following formulas. Example 135 uses a mixture of chlorpheniramine maleate and water with no emulsifier. The HLB value of the emulsifiers used in Examples 136–140 are listed in Table 17.

TABLE 17

(WEIGHT PERCENT)

|  | EX. 135 | EX. 136 | EX. 137 | EX. 138 | EX. 139 | EX. 140 |
|---|---|---|---|---|---|---|
| SUGAR | 54.7 | 54.7 | 54.7 | 54.7 | 54.7 | 54.7 |
| BASE | 19.2 | 19.2 | 19.2 | 19.2 | 19.2 | 19.2 |
| CORN SYRUP | 12.9 | 12.9 | 12.9 | 12.9 | 12.9 | 12.9 |
| GLYCERIN | 1.4 | 1.4 | 1.4 | 1.4 | 1.4 | 1.4 |
| DEXTROSE MONOHYDRATE | 9.9 | 9.9 | 9.9 | 9.9 | 9.9 | 9.9 |
| PEPP. FLAVOR | 0.9 | 0.9 | 0.9 | 0.9 | 0.9 | 0.9 |
| ACTIVE AGENT EMULSIFIER/ WATER MIXTURE | 1.0 | 1.0 | 1.0 | 1.0 | 1.0 | 1.0 |
|  | None | HLB = 2 | HLB = 4 | HLB = 6 | HLB = 9 | HLB = 12 |

Examples 141–146

The same as the formulations made in Examples 135–140, respectively, except that the flavor can be mixed together with the aqueous active agent solution and emulsified before adding the mixture to the gum batch.

The following Tables 18 through 25 are examples of gum formulations that demonstrate formula variations in which chlorpheniramine maleate may be used. The active agent may be added with or without encapsulation, or may be treated for fast release.

Examples 147–150 in Table 18 demonstrate the use of chlorpheniramine maleate in low-moisture sugar formulations showing less than 2% theoretical moisture:

TABLE 18

| | (WEIGHT PERCENT) | | | |
|---|---|---|---|---|
| | EX. 147 | EX. 148 | EX. 149 | EX. 150 |
| SUGAR | 58.77 | 58.51 | 58.77 | 54.51 |
| GUM BASE | 19.2 | 19.2 | 19.2 | 19.2 |
| CORN[a] SYRUP | 6.0 | 6.0 | — | — |
| DEXTROSE MONOHYDRATE | 10.0 | 10.0 | 10.0 | 10.0 |
| LACTOSE | 0.0 | 0.0 | 0.0 | 5.0 |
| GLYCERIN[b] | 5.0 | 5.0 | 11.0 | 10.0 |
| FLAVOR | 0.9 | 0.9 | 0.9 | 0.9 |
| ACTIVE CHLORPHENIRAMINE MALEATE | 0.13 | 0.39 | 0.13 | 0.39 |

[a]Corn syrup is evaporated to 85% solids, 15% moisture
[b]Glycerin and syrup may be blended and co-evaporated Examples 151–154 in Table 19 demonstrate the use of chlorpheniramine maleate in medium-moisture sugar formulations having about 2% to about 5% moisture.

Examples 155–158 in Table 20 demonstrate the use of chlorpheniramine maleate in high-moisture sugar formulations having more than about 5% moisture.

TABLE 19

| | (WEIGHT PERCENT) | | | |
|---|---|---|---|---|
| | EX. 151 | EX. 152 | EX. 153 | EX. 154 |
| SUGAR | 53.37 | 53.11 | 53.37 | 49.61 |
| GUM BASE | 19.2 | 19.2 | 19.2 | 19.2 |
| CORN SYRUP[a] | 15.0 | 15.0 | 13.0 | 12.5 |
| DEXTROSE MONOHYDRATE | 10.0 | 10.0 | 10.0 | 10.0 |
| GLYCERIN[b] | 1.4 | 1.4 | 3.4 | 7.4 |
| FLAVOR | 0.9 | 0.9 | 0.9 | 0.9 |
| ACTIVE CHLORPHENIRAMINE MALEATE | 0.13 | 0.39 | 0.13 | 0.39 |

[a]Corn syrup is evaporated to 85% solids, 15% moisture
[b]Glycerin and syrup may be blended and co-evaporated

TABLE 20

| | (WEIGHT PERCENT) | | | |
|---|---|---|---|---|
| | EX. 155 | EX. 156 | EX. 157 | EX. 158 |
| SUGAR | 50.87 | 50.51 | 49.87 | 49.61 |
| GUM BASE | 24.0 | 24.0 | 24.0 | 24.0 |
| CORN SYRUP | 24.0 | 24.0 | 24.0 | 24.6 |
| GLYCERIN | 0.0 | 0.0 | 1.0 | 0.4 |
| FLAVOR | 1.0 | 1.0 | 1.0 | 1.0 |
| ACTIVE CHLORPHENIRAMINE MALEATE | 0.13 | 0.39 | 0.13 | 0.39 |

Examples 159–162 in Table 21 and Examples 163–170 in Tables 22 and 23 demonstrate the use of chlorpheniramine maleate in low- and high-moisture gums that are sugar-free. Low-moisture gums have less than about 2% moisture, and high-moisture gums have greater than 2% moisture.

TABLE 21

| | (WEIGHT PERCENT) | | | |
|---|---|---|---|---|
| | EX. 159 | EX. 160 | EX. 161 | EX. 162 |
| BASE | 25.5 | 25.5 | 25.5 | 25.5 |
| SORBITOL | 50.87 | 50.61 | 48.87 | 45.61 |
| MANNITOL | 12.0 | 12.0 | 12.0 | 12.0 |
| GLYCERIN | 10.0 | 10.0 | 12.0 | 15.0 |
| FLAVOR | 1.5 | 1.5 | 1.5 | 1.5 |
| ACTIVE CHLORPHENIRAMINE MALEATE | 0.13 | 0.39 | 0.13 | 0.39 |

TABLE 22

| | (WEIGHT PERCENT) | | | |
|---|---|---|---|---|
| | EX. 163 | EX. 164 | EX. 165 | EX. 166 |
| BASE | 25.5 | 25.5 | 25.5 | 25.5 |
| SORBITOL | 50.87 | 50.61 | 40.87 | 40.61 |
| LIQUID SORBITOL* | 10.0 | 10.0 | 20.0 | 20.0 |
| MANNITOL | 10.0 | 10.0 | 10.0 | 10.0 |
| GLYCERIN | 2.0 | 2.0 | 2.0 | 2.0 |
| FLAVOR | 1.5 | 1.5 | 1.5 | 1.5 |
| ACTIVE CHLORPHENIRAMINE MALEATE | 0.13 | 0.39 | 0.13 | 0.39 |

*Sorbitol liquid contains 70% sorbitol, 30% water

TABLE 23

| | (WEIGHT PERCENT) | | | |
|---|---|---|---|---|
| | EX. 167 | EX. 168 | EX. 169 | EX. 170 |
| BASE | 25.5 | 25.5 | 25.5 | 25.5 |
| SORBITOL | 50.87 | 48.61 | 44.87 | 42.61 |
| HSH SYRUP* | 10.0 | 10.0 | 10.0 | 10.0 |
| MANNITOL | 8.0 | 8.0 | 8.0 | 8.0 |
| GLYCERIN** | 4.0 | 6.0 | 10.0 | 12.0 |
| FLAVOR | 1.5 | 1.5 | 1.5 | 1.5 |
| ACTIVE CHLORPHENIRAMINE MALEATE | 0.13 | 0.39 | 0.13 | 0.39 |

*Hydrogenated starch hydrolyzate syrup
**Glycerin and HSH syrup may be blended or co-evaporated Table 24 shows sugar chewing formulations that can be made with various types of sugars.

TABLE 24

(WEIGHT PERCENT)

| | EX. 171 | EX. 172 | EX. 173 | EX. 174 | EX. 175 | EX. 176 |
|---|---|---|---|---|---|---|
| GUM BASE | 19.2 | 19.2 | 19.2 | 19.2 | 19.2 | 19.2 |
| SUCROSE | 49.37 | 48.11 | 44.37 | 39.11 | 34.37 | 42.11 |
| GLYCERIN | 1.4 | 2.4 | 1.4 | 6.4 | 1.4 | 3.4 |
| CORN SYRUP | 14.0 | 14.0 | 14.0 | 14.0 | 14.0 | 14.0 |
| DEXTROSE | 5.0 | 5.0 | — | — | 10.0 | 5.0 |
| LACTOSE | 5.0 | 5.0 | 10.0 | 10.0 | — | — |
| FRUCTOSE | 5.0 | 5.0 | 10.0 | 10.0 | 10.0 | 5.0 |
| INVERT SUGAR | — | — | — | — | 10.0 | 10.0 |
| MALTOSE | — | — | — | — | — | — |
| CORN SYRUP SOLIDS | — | — | — | — | — | — |
| PEPPERMINT FLAVOR | 0.9 | 0.9 | 0.9 | 0.9 | 0.9 | 0.9 |
| ACTIVE CHLORPHEN-IRAMINE MALEATE | 0.13 | 0.39 | 0.13 | 0.39 | 0.13 | 0.39 |

| | EX. 177 | EX. 178 | EX. 179 | EX. 180 | EX. 181 | EX. 182 |
|---|---|---|---|---|---|---|
| GUM BASE | 19.2 | 19.2 | 19.2 | 19.2 | 19.2 | 19.2 |
| SUCROSE | 34.37 | 43.11 | 34.37 | 43.11 | 42.37 | 45.11 |
| GLYCERIN | 1.4 | 2.4 | 1.4 | 2.4 | 1.4 | 3.4 |
| CORN SYRUP | 14.0 | 14.0 | 14.0 | 14.0 | 11.0 | 11.0 |
| DEXTROSE | 10.0 | 5.0 | 10.0 | 5.0 | 10.0 | 5.0 |
| LACTOSE | — | — | — | — | — | — |
| FRUCTOSE | 10.0 | 5.0 | 10.0 | 5.0 | 5.0 | 5.0 |
| INVERT SUGAR | 10.0 | 10.0 | — | — | 5.0 | 5.0 |
| MALTOSE | — | — | 10.0 | 10.0 | — | — |
| CORN SYRUP SOLIDS | — | — | — | — | 5.0 | 5.0 |
| PEPPERMINT FLAVOR | 0.9 | 0.9 | 0.9 | 0.9 | 0.9 | 0.9 |
| ACTIVE CHLORPHENIRAMINE MALEATE | 0.13 | 0.39 | 0.13 | 0.39 | 0.13 | 0.39 |

Table 25 shows chewing gum formulations that are free of sugar. These formulations can use a wide variety of other non-sugar alditols.

TABLE 25

(WEIGHT PERCENT)

| | EX. 183 | EX. 184 | EX. 185 | EX. 186 | EX. 187 | EX. 188 |
|---|---|---|---|---|---|---|
| GUM BASE | 25.5 | 25.5 | 25.5 | 25.5 | 25.5 | 25.5 |
| GLYCERIN | 8.0 | 8.0 | 8.0 | 8.0 | 8.0 | 2.0 |
| SORBITOL | 47.87 | 37.611 | 37.87 | 32.61 | 31.87 | 29.61 |
| MANNITOL | — | 10.0 | 10.0 | 10.0 | 10.0 | 6.0 |
| SORBITOL LIQUID | 17.0 | 17.0 | — | — | — | — |
| LYCASIN | — | — | 17.0 | 12.0 | 8.0 | 20.0 |
| MALTITOL | — | — | — | 10.0 | — | — |
| XYLITOL | — | — | — | — | 15.0 | 15.0 |
| LACTITOL | — | — | — | — | — | — |
| PALATINIT | — | — | — | — | — | — |
| FLAVOR | 1.5 | 1.5 | 1.5 | 1.5 | 1.5 | 1.5 |
| ACTIVE CHLORPHENIRAMINE MALEATE | 0.13 | 0.39 | 0.13 | 0.39 | 0.13 | 0.39 |

| | EX. 189 | EX. 190 | EX. 191 | EX. 192 | EX. 193 | EX. 194 |
|---|---|---|---|---|---|---|
| GUM BASE | 25.5 | 25.5 | 25.5 | 25.5 | 25.5 | 25.5 |
| GLYCERIN | 8.0 | 8.0 | 8.0 | 2.0 | 8.0 | 2.0 |
| SORBITOL | 41.87 | 36.61 | 31.87 | 40.61 | 29.87 | 29.61 |
| MANNITOL | 8.0 | 8.0 | 8.0 | — | — | — |
| SORBITOL LIQUID | 5.0 | — | — | — | — | — |
| LYCASIN | — | 5.0 | 5.0 | 5.0 | 10.0 | 20.0 |
| MALTITOL | — | 5.0 | — | — | — | — |

TABLE 25-continued (WEIGHT PERCENT)

| | | | | | | |
|---|---|---|---|---|---|---|
| XYLITOL | — | — | — | 15.0 | 15.0 | 11.0 |
| LACTITOL | 10.0 | 10.0 | 10.0 | — | — | — |
| PALATINIT | — | — | 10.0 | 10.0 | 10.0 | 10.0 |
| FLAVOR | 1.5 | 1.5 | 1.5 | 1.5 | 1.5 | 1.5 |
| ACTIVE CHLORPHENIRAMINE MALEATE | 0.13 | 0.39 | 0.13 | 0.39 | 0.13 | 0.39 |

High-intensity sweeteners (HIS) such as aspartame, acesulfame K, or the salts of acesulfame, cyclamate and its salts, saccharin and its salts, alitame, neotame, sucralose, thaumatin, monellin, dihydrochalcone, stevioside, glycyrrhizin, and combinations thereof may be used in any of the Examples listed in Tables 18–25. Since chlorpheniramine maleate may reduce sweetness, HIS may be used in sugar gum, and some of the alditols in sugar-free gum are less sweet than sugar so higher levels of HIS may be needed to obtain the proper level of sweetness.

High-intensity sweeteners (HIS) may also be modified to control their release in those chewing gum formulations. This can be controlled by various methods of encapsulation, agglomeration, absorption, or a combination of methods to obtain either a fast or slow release of the sweetener. Sweetener combinations, some of which may be synergistic, may also be included in the gum formulations.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 26. Gum center formulas may or may not contain chlorpheniramine maleate.

Formulations with or without active chlorpheniramine maleate can also be made similar to those found in Tables 18–23 for low, medium, and high moisture formulas. Higher levels of base may be used with a corresponding decrease in other ingredients. Also, other sugars are polyols may be used in the gum center as found in Tables 24 and 25. Chlorpheniramine maleate may be added to a gum center only, or to a gum coating with none in the center, or to both center and coating. Coated gum pieces are about 1.5 grams, so to obtain 4 mg of chlorpheniramine maleate total piece must contain 0.27%.

Chlorpheniramine maleate can be used in the coating formula on the various pellet gum formulations. The following Table 27 shows some sugar and dextrose type formulas:

TABLE 27

(DRY WEIGHT PERCENT)

| | EX. 201 | EX. 202 | EX. 203 | EX. 204 | EX. 205 | EX. 206 |
|---|---|---|---|---|---|---|
| SUGAR | 97.1 | 95.13 | 93.29 | 96.9 | 94.83 | 92.79 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| CHLORPHEN-IRAMINE MALEATE | — | 0.27 | 0.81[a] | — | 0.27 | 0.81[a] |

| | EX. 207 | EX. 208 | EX. 209 | EX. 210 |
|---|---|---|---|---|
| DEXTROSE MONOHYDRATE | 97.6 | 95.13 | 96.93 | 93.69 |
| GUM ARABIC | 1.5 | 3.0 | 1.5 | 3.0 |

TABLE 26

(WEIGHT PERCENT)

| | EX. 195 | EX. 196 | EX. 197 | EX. 198 | EX. 199 | EX. 200 |
|---|---|---|---|---|---|---|
| SUGAR | 52.0 | 48.73 | 47.59 | 44.0 | 40.73 | 38.59 |
| GUM BASE | 26.0 | 30.0 | 35.00 | 26.0 | 30.0 | 35.00 |
| CORN SYRUP | 20.0 | 19.0 | 15.00 | 18.0 | 17.0 | 14.00 |
| GLYCERIN | 1.0 | 1.0 | 1.00 | 1.0 | 1.0 | 1.00 |
| PEPPERMINT FLAVOR | 1.0 | 1.0 | 1.00 | 1.0 | 1.0 | 1.00 |
| DEXTROSE MONOHYDRATE | — | — | — | 10.0 | 10.0 | 10.00 |
| ACTIVE CHLORPHENIRAMINE MALEATE | —[a] | 0.27 | 0.41 | —[a] | 0.27 | 0.41 |

[a]All of the active agent is in the coating, which comprises 33% of the product.

TABLE 27-continued (DRY WEIGHT PERCENT)

| | | | | |
|---|---|---|---|---|
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| CHLORPHENIRAMINE MALEATE | — | 0.27 | 0.27 | 0.81[a] |

[a]All of the active agent is in the coating, which comprises 33% ot the product.

The above formulations are made by making a syrup by dissolving the sugar and gum arabic in solution at about 75% solids at boiling, and suspending titanium dioxide or calcium carbonate in this syrup. Some of the dextrose may be added as a dry charge, which may also contain the active. Chlorpheniramine maleate may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Chlorpheniramine maleate may be dissolved in flavor and added to the coating. After the final coats are applied and dried, wax is applied to give a smooth polish.

Chlorpheniramine maleate may also be used in coating of sugarless gum centers. Like sugar gum centers, the base formulation can be increased in proportion to the amount of coating applied to the center. Formulations with and without chlorpheniramine maleate similar to those found in Tables 21–25 for low and high moisture gum can be used to make gum centers. Generally, the base level may be increased to 30–46% with the other ingredients proportionally reduced. Some typical gum formulas are in Table 28.

TABLE 28

WEIGHT PERCENT)

| | EX. 211 | EX. 212 | EX. 213 | EX. 214 | EX. 215 | EX. 216 | EX. 217 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 45.03 | 45.89 | 40.3 | 44.53 | 41.29 | 25.96 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| ACTIVE CHLORPHEN-IRAMINE MALEATE[b] | —[c] | 0.27 | 0.41 | —[c] | 0.27 | 0.41 | 0.54[d] |

[a]Lycasin brand hydrogenated starch hydrolyzate used instead of sorbitol liquid
[b]This material may be dissolved in water, glycerin, sorbitol liquid, or HSH.
[c]All of th active agent is in the coating, which comprises 33% of the product.
[d]This example required 50% of the product to be a coating with no active agent in the coating, to give a gum product with 0.27% active agent.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, lactitol and hydrogenated isomaltulose may also be used in the gum center formulations at various levels similar to those shown in Table 25. The texture may be adjusted by varying glycerin or sorbitol liquid. Sweetness of the center formulation can also be adjusted by varying the level of high intensity sweetener.

Chlorpheniramine maleate may be used in sugarless coatings with xylitol, sorbitol, maltitol, lactitol, hydrogenated isomaltulose and erythritol. The following table gives formulas for a xylitol coating:

TABLE 29

(DRY WEIGHT PERCENT)

| | EX. 218 | EX. 219 | EX. 220 | EX. 221 | EX. 222 | EX. 223 |
|---|---|---|---|---|---|---|
| XYLITOL | 94.8 | 92.13 | 89.89 | 90.1 | 89.63 | 87.99 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| CHLORPHEN-IRAMINE MALEATE | — | 0.27 | 0.81[a] | — | 0.27 | 0.81[a] |

*Lake color dispersed in xylitol solution
**Calcium carbonate used in place of titanium dioxide
[a]All of the active agent is in the coating, which comprises 33% of the product.

The above formulas are used to coat pellets by applying a xylitol/gum arabic solution in multiple coats and air drying. Color or whitener is also mixed in the solution. Chlorpheniramine maleate may be dissolved in water or flavor and added between coating applications or mixed with the hot syrup and used in the early stages of coating or used throughout the coating process. After pellets have been coated and dried, talc and wax are added to give a polish.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 30

(DRY WEIGHT PERCENT)

| | EX. 224 | EX. 225 | EX. 226 | EX. 227 | EX. 228 | EX. 229 |
|---|---|---|---|---|---|---|
| MALTITOL | 96.8 | 94.63 | 91.29 | 86.8 | 75.83 | 68.69 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| CHLORPHEN-IRAMINE MALEATE | — | 0.27 | 0.81[a] | — | 0.27 | 0.81[a] |

[a] All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Chlorpheniramine maleate may be applied in a similar manner as in the previous xylitol coating, or may be preblended with the dry charge material.

In a similar manner, coatings with sorbitol, lactitol, and hydrogenated isomaltulose may be made in the coating formulas in Table 30 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like dyclonine hydrochloride, gum talha, gum arabic or other moisture absorbing materials. Also, powdered sweeteners or flavors could be added with the dry charge.

Some polyols such as sorbitol, maltitol, lactitol, erythritol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

The formulas listed in Table 31 comprise various sugar-type formulas in which active medicament can be added to gum after it is dissolved in water or mixed with various aqueous solvents. Pseudoephedrine hydrochloride (Sudafed™) is an active medicament used as a nasal decongestant. These formulas give a 3 gram stick with 30 mg of pseudoephedrine hydrochloride.

TABLE 31

(WEIGHT PERCENT)

| | EX. 230 | EX. 231 | EX. 232 | EX. 233 | EX. 234 | EX. 235 | EX. 236 | EX. 237 |
|---|---|---|---|---|---|---|---|---|
| SUGAR | 64.6 | 64.0 | 61.0 | 67.0 | 63.0 | 53.0 | 60.7 | 47.0 |
| BASE | 19.2 | 19.2 | 19.2 | 19.2 | 19.2 | 19.2 | 19.2 | 19.2 |
| CORN SYRUP | 12.9 | 10.9 | 8.9 | 2.9 | 6.9 | 6.9 | 0.0 | 2.9 |
| PEPPERMINT FLAVOR | 0.9 | 0.9 | 0.9 | 0.9 | 0.9 | 0.0 | 0.9 | 0.9 |
| GLYCERIN | 1.4 | 0.0 | 0.0 | 0.0 | 0.0 | 0.9 | 1.4 | 0.0 |
| LIQUID/ACTIVE BLEND | 1.0 | 5.0 | 10.0 | 10.0 | 10.0 | 20.0 | 17.8 | 30.0 |

Example 230

Pseudoephedrine hydrochloride powder can be added directly to the gum.

Example 231

A 20 gram quantity of pseudoephedrine hydrochloride can be dissolved in 80 grams of water giving a 20% solution and added to gum.

Example 232

A 10 gram quantity of pseudoephedrine hydrochloride can be dissolved in 50 grams of water and mixed with 50 grams of glycerin and added to the gum.

Example 233

A 10 gram quantity of pseudoephedrine hydrochloride is mixed with 90 grams of glycerin giving a 10% solution and added to gum.

Example 234

A 10 gram quantity of pseudoephedrine hydrochloride is mixed with 90 grams of propylene glycol giving a 10% solution and added to gum.

Example 235

A 10 gram quantity of pseudoephedrine hydrochloride is dissolved in grams of peppermint flavor and added to gum.

Example 236

A 10 gram quantity of pseudoephedrine hydrochloride is dissolved in 168 grams of corn syrup and added to chewing gum.

Example 237

To a 200 gram quantity of corn syrup is added 100 grams of glycerin. To this mixture is added 10 gram of pseudoephedrine hydrochloride and blended. This mixture is then added to gum.

In the next examples of sugar formulations, pseudoephedrine hydrochloride can be dissolved in water and emulsifiers can be added to the aqueous solution. Example solutions can be prepared by dissolving 20 grams of pseudoephedrine hydrochloride in 65 grams of water and adding 15 grams of emulsifiers of various hydrophilic-lipophilic balance (HLB) values to the solution. The mixtures can then be used in the following formulas. Example 238 uses a mixture of pseudoephedrine hydrochloride and water with no emulsifier. The HLB value of the emulsifiers used in Examples 238–243 are listed in Table 32.

TABLE 32

| | (WEIGHT PERCENT) | | | | | |
|---|---|---|---|---|---|---|
| | EX. 238 | EX. 239 | EX. 240 | EX. 241 | EX. 242 | EX. 243 |
| SUGAR | 50.7 | 50.7 | 50.7 | 50.7 | 50.7 | 50.7 |
| BASE | 19.2 | 19.2 | 19.2 | 19.2 | 19.2 | 19.2 |
| CORN SYRUP | 12.9 | 12.9 | 12.9 | 12.9 | 12.9 | 12.9 |
| GLYCERIN | 1.4 | 1.4 | 1.4 | 1.4 | 1.4 | 1.4 |
| DEXTROSE MONO-HYDRATE | 9.9 | 9.9 | 9.9 | 9.9 | 9.9 | 9.9 |
| PEPP. FLAVOR | 0.9 | 0.9 | 0.9 | 0.9 | 0.9 | 0.9 |
| ACTIVE AGENT EMULSIFIER/ WATER MIXTURE | 5.0 | 5.0 | 5.0 | 5.0 | 5.0 | 5.0 |
| | None | HLB = 2 | HLB = 4 | HLB = 6 | HLB = 9 | HLB = 12 |

The formulations made in Examples 238–243 can be changed in that the flavor can be mixed together with the aqueous active agent solution and emulsified before adding the mixture to the gum batch.

The following Tables 33 through 40 are examples of gum formulations that demonstrate formula variations in which pseudoephedrine hydrochloride may be used. The active agent may be added with or without encapsulation or may be treated for fast release.

Examples 244–247 in Table 33 demonstrate the use of pseudoephedrine hydrochloride in low-moisture sugar formulations showing less than 2% theoretical moisture:

TABLE 33

| | (WEIGHT PERCENT) | | | |
|---|---|---|---|---|
| | EX. 244 | EX. 245 | EX. 246 | EX. 247 |
| SUGAR | 57.9 | 55.9 | 57.9 | 50.9 |
| GUM BASE | 19.2 | 19.2 | 19.2 | 19.2 |

TABLE 33-continued

| | (WEIGHT PERCENT) | | | |
|---|---|---|---|---|
| | EX. 244 | EX. 245 | EX. 246 | EX. 247 |
| CORN[a] SYRUP | 6.0 | 6.0 | — | — |
| DEXTROSE MONO-HYDRATE | 10.0 | 10.0 | 10.0 | 10.0 |
| LACTOSE | 0.0 | 0.0 | 0.0 | 5.0 |
| GLYCERIN[b] | 5.0 | 5.0 | 11.0 | 11.0 |
| FLAVOR | 0.9 | 0.9 | 0.9 | 0.9 |
| ACTIVE PSEUDO-EPHEDRINE HYDRO CHLORIDE | 1.0 | 3.0 | 1.0 | 3.0 |

[a]Corn syrup is evaporated to 85% solids, 15% moisture
[b]Glycerin and syrup may be blended and co-evaporated Examples 248–251 in Table 34 demonstrate the use of pseudoephedrine hydrochloride in medium-moisture sugar formulations having about 2% to about 5% moisture.

Examples 252–255 in Table 35 demonstrate the use of pseudoephedrine hydrochloride in high-moisture sugar formulations having more than about 5% moisture.

TABLE 34

| | (WEIGHT PERCENT) | | | |
|---|---|---|---|---|
| | EX. 248 | EX. 249 | EX. 250 | EX. 251 |
| SUGAR | 52.5 | 50.5 | 52.5 | 49.0 |
| GUM BASE | 19.2 | 19.2 | 19.2 | 19.2 |
| CORN SYRUP[a] | 15.0 | 15.0 | 13.0 | 12.5 |
| DEXTROSE MONO-HYDRATE | 10.0 | 10.0 | 10.0 | 10.0 |
| GLYCERIN[b] | 1.4 | 1.4 | 3.4 | 5.4 |
| FLAVOR | 0.9 | 0.9 | 0.9 | 0.9 |
| ACTIVE PSEUDO-EPHEDRINE HYDRO CHLORIDE | 1.0 | 3.0 | 1.0 | 3.0 |

[a]Corn syrup is evaporated to 85% solids, 15% moisture
[b]Glycerin and syrup may be blended and co-evaporated

TABLE 35

| | (WEIGHT PERCENT) | | | |
|---|---|---|---|---|
| | EX. 252 | EX. 253 | EX. 254 | EX. 255 |
| SUGAR | 50.0 | 48.0 | 49.0 | 47.0 |
| GUM BASE | 24.0 | 24.0 | 24.0 | 24.0 |
| CORN SYRUP | 24.0 | 24.0 | 24.0 | 24.6 |
| GLYCERIN | 0.0 | 0.0 | 1.0 | 0.4 |
| FLAVOR | 1.0 | 1.0 | 1.0 | 1.0 |
| ACTIVE PSEUDO-EPHEDRINE HYDROCHLORIDE | 1.0 | 3.0 | 1.0 | 3.0 |

Examples 256–259 in Table 36 and Examples 260–267 in Tables 37 and 38 demonstrate the use of pseudoephedrine hydrochloride in low- and high-moisture gums that are sugar-free. Low-moisture gums have less than about 2% moisture, and high-moisture gums have greater than 2% moisture.

TABLE 36

| | (WEIGHT PERCENT) | | | |
|---|---|---|---|---|
| | EX. 256 | EX. 257 | EX. 258 | EX. 259 |
| BASE | 25.5 | 25.5 | 25.5 | 25.5 |
| SORBITOL | 50.0 | 48.0 | 48.0 | 43.0 |
| MANNITOL | 12.0 | 12.0 | 12.0 | 12.0 |
| GLYCERIN | 10.0 | 10.0 | 12.0 | 15.0 |
| FLAVOR | 1.5 | 1.5 | 1.5 | 1.5 |
| ACTIVE PSEUDO-EPHEDRINE HYDROCHLORIDE | 1.0 | 3.0 | 1.0 | 3.0 |

TABLE 37

| | (WEIGHT PERCENT) | | | |
|---|---|---|---|---|
| | EX. 260 | EX. 261 | EX. 262 | EX. 263 |
| BASE | 25.5 | 25.5 | 25.5 | 25.5 |
| SORBITOL | 50.0 | 48.0 | 40.0 | 38.0 |
| LIQUID SORBITOL* | 10.0 | 10.0 | 20.0 | 20.0 |
| MANNITOL | 10.0 | 10.0 | 10.0 | 10.0 |
| GLYCERIN | 2.0 | 2.0 | 2.0 | 2.0 |
| FLAVOR | 1.5 | 1.5 | 1.5 | 1.5 |
| ACTIVE PSEUDO-EPHEDRINE HYDROCHLORIDE | 1.0 | 3.0 | 1.0 | 3.0 |

*Sorbitol liquid contains 70% sorbitol, 30% water

TABLE 38

| | (WEIGHT PERCENT) | | | |
|---|---|---|---|---|
| | EX. 264 | EX. 265 | EX. 266 | EX. 267 |
| BASE | 25.5 | 25.5 | 25.5 | 25.5 |
| SORBITOL | 50.0 | 46.0 | 44.0 | 42.0 |
| HSH SYRUP* | 10.0 | 10.0 | 10.0 | 10.0 |
| MANNITOL | 8.0 | 8.0 | 8.0 | 8.0 |
| GLYCERIN** | 4.0 | 6.0 | 10.0 | 10.0 |
| FLAVOR | 1.5 | 1.5 | 1.5 | 1.5 |
| ACTIVE PSEUDO-EPHEDRINE HYDROCHLORIDE | 1.0 | 3.0 | 1.0 | 3.0 |

*Hydrogenated starch hydrolyzate syrup
**Glycerin and HSH syrup may be blended or co-evaporated Table 39 shows sugar chewing formulations that can be made with various types of sugars.

TABLE 39

| | (WEIGHT PERCENT) | | | | | | | | | | | |
|---|---|---|---|---|---|---|---|---|---|---|---|---|
| | EX. 268 | EX. 269 | EX. 270 | EX. 271 | EX. 272 | EX. 273 | EX. 274 | EX. 275 | EX. 276 | EX. 277 | EX. 278 | EX. 279 |
| GUM BASE | 19.2 | 19.2 | 19.2 | 19.2 | 19.2 | 19.2 | 19.2 | 19.2 | 19.2 | 19.2 | 19.2 | 19.2 |
| SUCROSE | 48.5 | 44.5 | 43.5 | 39.5 | 33.5 | 39.5 | 33.5 | 39.5 | 33.5 | 39.5 | 41.5 | 42.5 |
| GLYCERIN | 1.4 | 3.4 | 1.4 | 3.4 | 1.4 | 3.4 | 1.4 | 3.4 | 1.4 | 3.4 | 1.4 | 3.4 |
| CORN SYRUP | 14.0 | *14.0 | 14.0 | 14.0 | 14.0 | 14.0 | 14.0 | 14.0 | 14.0 | 14.0 | 11.0 | 11.0 |
| DEXTROSE | 5.0 | 5.0 | — | — | 10.0 | 5.0 | 10.0 | 5.0 | 10.0 | 5.0 | 10.0 | 5.0 |
| LACTOSE | 5.0 | 5.0 | 10.0 | 10.0 | — | — | — | — | — | — | — | — |
| FRUCTOSE | 5.0 | 5.0 | 10.0 | 10.0 | 10.0 | 5.0 | 10.0 | 5.0 | 10.0 | 5.0 | 5.0 | 5.0 |
| INVERT SUGAR | — | — | — | — | 10.0 | 10.0 | 10.0 | 10.0 | — | — | 5.0 | 5.0 |
| MALTOSE | — | — | — | — | — | — | — | — | 10.0 | 10.0 | — | — |
| CORN SYRUP SOLIDS | — | — | — | — | — | — | — | — | — | — | 5.0 | 5.0 |
| PEPPERMINT FLAVOR | 0.9 | 0.9 | 0.9 | 0.9 | 0.9 | 0.9 | 0.9 | 0.9 | 0.9 | 0.9 | 0.9 | 0.9 |
| ACTIVE PSEUDO-EPHEDRINE HYDRO-CHLORIDE | 1.0 | 3.0 | 1.0 | 3.0 | 1.0 | 3.0 | 1.0 | 3.0 | 1.0 | 3.0 | 1.0 | 3.0 |

Table 40 shows chewing gum formulations that are free of sugar. These formulations can use a wide variety of other non-sugar alditols.

TABLE 40

| | (WEIGHT PERCENT) | | | | | | | | | | | |
|---|---|---|---|---|---|---|---|---|---|---|---|---|
| | EX. 280 | EX. 281 | EX. 282 | EX. 283 | EX. 284 | EX. 285 | EX. 286 | EX. 287 | EX. 288 | EX. 289 | EX. 290 | EX. 291 |
| GUM BASE | 25.5 | 25.5 | 25.5 | 25.5 | 25.5 | 25.5 | 25.5 | 25.5 | 25.5 | 25.5 | 25.5 | 25.5 |
| GLYCERIN | 8.0 | 8.0 | 8.0 | 8.0 | 8.0 | 2.0 | 8.0 | 8.0 | 8.0 | 2.0 | 8.0 | 2.0 |
| SORBITOL | 47.0 | 35.0 | 37.0 | 30.0 | 31.0 | 27.0 | 41.0 | 34.0 | 31.0 | 38.0 | 29.0 | 38.0 |
| MANNITOL | — | 10.0 | 10.0 | 10.0 | 10.0 | 6.0 | 8.0 | 8.0 | 8.0 | — | — | — |
| SORBITOL LIQUID | 17.0 | 17.0 | — | — | — | — | 5.0 | — | — | — | — | — |
| LYCASIN | — | — | 17.0 | 2.0 | 8.0 | 20.0 | — | 5.0 | 5.0 | 5.0 | 10.0 | 20.0 |
| MALTITOL | — | — | — | 10.0 | — | — | — | 5.0 | — | — | — | — |
| XYLITOL | — | — | — | — | 15.0 | 15.0 | — | — | — | 15.0 | 15.0 | — |
| LACTITOL | — | — | — | — | — | — | 10.0 | 10.0 | 10.0 | — | — | — |
| PALATINIT | — | — | — | — | — | — | — | — | 10.0 | 10.0 | 10.0 | 10.0 |
| FLAVOR | 1.5 | 1.5 | 1.5 | 1.5 | 1.5 | 1.5 | 1.5 | 1.5 | 1.5 | 1.5 | 1.5 | 1.5 |
| ACTIVE PSEUDO-EPHEDRINE HYDRO-CHLORIDE | 1.0 | 3.0 | 1.0 | 3.0 | 1.0 | 3.0 | 1.0 | 3.0 | 1.0 | 3.0 | 1.0 | 3.0 |

High-intensity sweeteners (HIS) such as aspartame, acesulfame K, or the salts of acesulfame, cyclamate and its salts, saccharin and its salts, alitame, neotame, sucralose, thaumatin, monellin, dihydrochalcone, stevioside, glycyrrhizin, and combinations thereof may be used in any of the Examples listed in Tables 33–40. Since pseudoephedrine hydrochloride may reduce sweetness, HIS may be used in sugar gum, and some of the alditols in sugar-free gum are less sweet than sugar so higher levels of HIS may be needed to obtain the proper level of sweetness.

High-intensity sweeteners (HIS) may also be modified to control their release in those chewing gum formulations. This can be controlled by various methods of encapsulation, agglomeration, absorption, or a combination of methods to obtain either a fast or slow release of the sweetener. Sweetener combinations, some of which may be synergistic, may also be included in the gum formulations.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type-gum center formulations are shown in Table 41 containing pseudoephedrine hydrochloride, which is a nasal decongestant as an active medicament.

TABLE 41

| | (WEIGHT PERCENT) | | | | | |
|---|---|---|---|---|---|---|
| | EX. 292 | EX. 293 | EX. 294 | EX. 295 | EX. 296 | EX. 297 |
| SUGAR | 52.0 | 48.0 | 46.5 | 44.0 | 40.0 | 37.5 |
| GUM BASE | 26.0 | 30.0 | 35.0 | 26.0 | 30.0 | 35.0 |
| CORN SYRUP | 20.0 | 19.0 | 15.00 | 18.0 | 17.0 | 14.00 |
| GLYCERIN | 1.0 | 1.0 | 1.00 | 1.0 | 1.0 | 1.00 |
| PEPPERMINT FLAVOR | 1.0 | 1.0 | 1.00 | 1.0 | 1.0 | 1.00 |
| DEXTROSE MONO-HYDRATE | — | — | — | 10.0 | 10.0 | 10.00 |
| ACTIVE PSEUDO-EPHEDRINE HYDRO-CHLORIDE | —[a] | 1.0 | 1.5 | —[a] | 1.0 | 1.5 |

[a]All of the active agent is in the coating, which comprises 33% of the product.

Formulations with or without active pseudoephedrine hydrochloride can also be made similar to those found in Tables 33–38 for low, medium, and high moisture formulas. Higher levels of base may be used with a corresponding decrease in other ingredients. Also, other sugars are polyols may be used in the gum center as found in Tables 39 and 40. Pseudoephedrine hydrochloride may be added to a gum center only, or to a gum coating with none in the center, or to both center and coating. Coated gum pieces are about 1.5 grams per piece, so to obtain 30 mg of pseudoephedrine hydrochloride in two gum pieces, total piece must contain 1.0%.

Pseudoephedrine hydrochloride can be used in the coating formula on the various pellet gum formulations. The following Table 42 shows some sugar and dextrose type formulas:

TABLE 42

(DRY WEIGHT PERCENT)

| | EX. 298 | EX. 299 | EX. 300 | EX. 301 | EX. 302 | EX. 303 |
|---|---|---|---|---|---|---|
| SUGAR | 97.1 | 94.4 | 91.1 | 96.9 | 94.1 | 90.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| PSEUDO-EPHEDRINE HYDROCHLORIDE | — | 1.0 | 3.0$^a$ | — | 1.0 | 3.0$^a$ |

| | EX. 304 | EX. 305 | EX. 306 | EX. 307 |
|---|---|---|---|---|
| DEXTROSE MONOHYDRATE | 97.6 | 94.4 | 96.2 | 91.5 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| PSEUDO-EPHEDRINE HYDROCHLORIDE | — | 1.0 | 1.0 | 3.0$^a$ |

$^a$All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. Pseudoephedrine hydrochloride may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Pseudoephedrine hydrochloride may be dissolved in flavor and added to the coating. After the final coats are applied and dried, wax is applied to give a smooth polish.

As shown in Table 43, some of the sugar or dextrose may be added as a dry charge, which may also contain the active.

TABLE 43

(DRY WEIGHT PERCENT)

| | EX. 308 | EX. 309 | EX. 310 | EX. 311 | EX. 312 | EX. 313 |
|---|---|---|---|---|---|---|
| SUGAR | 76.5 | 78.4 | — | — | 86.5 | — |
| DEXTROSE MONOHYDRATE | — | — | 76.5 | 83.3 | — | 84.1 |
| POWDER SUGAR* | 20.0 | 15.0 | — | — | — | — |
| POWDER DEXTROSE* | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| PSEUDO-EPHEDRINE HYDROCHLORIDE | 1.0 | 3.0$^a$ | 1.0 | 3.0$^a$ | 1.0 | 3.0$^a$ |

*Powder and/or crystalline sugar may be used.
$^a$All of the active agent is in the coating, which comprises 33% of the product.

In Examples 308–311 gum arabic powder is blended in the sugar syrup. In Examples 312 and 313, gum arabic powder is dry charged after a gum arabic solution is applied in the first stages of coating, then this is followed by a hard shell coating of sugar solution or dextrose solution.

Pseudoephedrine hydrochloride may also be used in coating of sugarless gum centers. Like sugar gum centers, the base formulation can be increased in proportion to the amount of coating applied to the center. Formulations with and without pseudoephedrine hydrochloride similar to those found in Tables 33–38 for low and high moisture gum can be used to make gum centers. Generally, the base level may be increased to 30–46% with the other ingredients proportionally reduced. Some typical gum formulas are in Table 44.

TABLE 44

(WEIGHT PERCENT)

| | EX. 314 | EX. 315 | EX. 316 | EX. 317 | EX. 318 | EX. 319 | EX. 320 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.3 | 44.8 | 40.3 | 43.8 | 40.2 | 24.5 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0$^{a)}$ | 10.0$^{a)}$ |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |

TABLE 44-continued (WEIGHT PERCENT)

|  | EX. 314 | EX. 315 | EX. 316 | EX. 317 | EX. 318 | EX. 319 | EX. 320 |
|---|---|---|---|---|---|---|---|
| ACTIVE PSEUDO-EPHEDRINE HYDRO-CHLORIDE[b] | —[c] | 1.0 | 1.5 | —[c] | 1.0 | 1.5 | 2.0[d] |

[a] Lycasin brand hydrogenated starch hydrolyzate used instead of sorbitol liquid
[b] This material may be dissolved in water, glycerin, sorbitol liquid, or HSH.
[c] All of the active agent is in the coating, which comprises 33% of the product.
[d] This example required 50% of the product to be a coating with no active agent in the coating, to give a gum product with 1% active agent.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, erythritol, xylitol, lactitol and hydrogenated isomaltulose may also be used in the gum center formulations at various levels similar to those shown in Table 40. The texture may be adjusted by varying glycerin or sorbitol liquid. Sweetness of the center formulation can also be adjusted by varying the level of high intensity sweetener.

Pseudoephedrine hydrochloride may be used in sugarless coatings with xylitol, sorbitol, maltitol, lactitol, hydrogenated isomaltulose and erythritol. The following table gives formulas for a xylitol coating:

TABLE 45

(DRY WEIGHT PERCENT)

|  | EX. 321 | EX. 322 | EX. 323 | EX. 324 | EX. 325 | EX. 326 |
|---|---|---|---|---|---|---|
| XYLITOL | 94.8 | 91.4 | 87.7 | 90.1 | 88.9 | 85.8 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| PSEUDO-EPHEDRINE HYDRO-CHLORIDE | — | 1.0 | 3.0[a] | — | 1.0 | 3.0[a] |

*Lake color dispersed in xylitol solution
**Calcium carbonate used in place of titanium dioxide
[a] All of the active agent is in the coating, which comprises 33% of the product.

The above formulas are used to coat pellets by applying a xylitol/gum arabic solution in multiple coats and air drying. Color or whitener is also mixed in the solution. Pseudoephedrine hydrochloride may be dissolved in water or flavor and added between coating applications or mixed with the hot syrup and used in the early stages of coating or used throughout the coating process. After pellets have been coated and dried, talc and wax are added to give a polish.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 46

(DRY WEIGHT PERCENT)

|  | EX. 327 | EX. 328 | EX. 329 | EX. 330 | EX. 331 | EX. 332 |
|---|---|---|---|---|---|---|
| MALTITOL | 96.8 | 93.9 | 89.1 | 86.8 | 75.1 | 68.5 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| PSEUDO-EPHEDRINE HYDRO-CHLORIDE | — | 1.0 | 3.0[a] | — | 1.0 | 3.0[a] |

[a] All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Pseudoephedrine hydrochloride may be applied in a similar manner as in the previous xylitol coating examples, or may be preblended with the dry charge material.

In a similar manner, coatings with sorbitol, lactitol, and hydrogenated isomaltulose may be made in the coating formulas in Table 46 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, lactitol, erythritol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 47 in which cetyl pyridimium chloride (CPC) can be added as the active medicament. This medicament can be used as an oral antimicrobial to reduce oral malodor and reduce oral bacteria. These formulas give a 1.5 gram piece containing 5 mg of CPC or 0.33%. Gum center formulas may or may not contain CPC, which has been encapsulated for controlled release.

TABLE 47

(WEIGHT PERCENT)

| | EX. 333 | EX. 334 | EX. 335 | EX. 336 | EX. 337 | EX. 338 |
|---|---|---|---|---|---|---|
| SUGAR | 52.0 | 48.67 | 47.5 | 44.0 | 40.67 | 38.5 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONO-HYDRATE | — | — | — | 10.0 | 10.0 | 10.0 |
| ACTIVE CPC | —[a] | 0.33 | 0.5 | —[a] | 0.33 | 0.5 |

[a]All of the active agent is in the coating, which comprises 33% of the product Formulations with or without CPC can also be made similar to those found in previous tables for low, medium, and high moisture formulas. Higher levels of base may be used with a corresponding decrease in other ingredients. Also, other sugars and polyols may be used in the gum center as found in previous tables. Cetyl pyridimium chloride may be added to a gum center only, into a gum coating with more in the center or to both center and coating.

CPC can be used in the coating formula on the various pellet gum formulations. The following Table 48 shows some sugar and dextrose type formulas:

TABLE 48

(DRY WEIGHT PERCENT)

| | EX. 339 | EX. 340 | EX. 341 | EX. 342 | EX. 343 | EX. 344 |
|---|---|---|---|---|---|---|
| SUGAR | 97.1 | 95.07 | 93.1 | 96.9 | 94.77 | 92.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| CPC | — | 0.33 | 1.0[a] | — | 0.33 | 1.0[a] |

| | EX. 345 | EX. 346 | EX. 347 | EX. 348 |
|---|---|---|---|---|
| DEXTROSE MONO-HYDRATE | 97.6 | 95.07 | 96.87 | 93.5 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| CPC | — | 0.33 | 0.33 | 1.0[a] |

[a]All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. CPC may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. CPC may also be premixed with the flavor. After the final coats are applied and dried, wax is applied to give a smooth polish.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. CPC may be added dry to the coating with the dry charge material. Table 49 gives these types of formulas.

TABLE 49

(DRY WEIGHT PERCENT)

| | EX. 349 | EX. 350 | EX. 351 | EX. 352 | EX. 353 | EX. 354 |
|---|---|---|---|---|---|---|
| SUGAR | 77.17 | 80.4 | — | — | 87.17 | — |
| DEXTROSE MONO-HYDRATE | — | — | 77.17 | 85.3 | — | 86.1 |
| POWDER SUGAR* | 20.0 | 15.0 | — | — | — | — |
| POWDER DEXTROSE | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| CPC | 0.33 | 1.0[a] | 0.33 | 1.0[a] | 0.33 | 1.0[a] |

*Powder and/or crystalline sugar may be used.
[a]All of the active agent is in the coating, which comprises 33% of the product.

In Examples 349–352, gum arabic is blended in the sugar syrup. In Examples 353 and 354, gum arabic powder is dry charged after gum arabic solution is applied in the first stages of coating, then this is followed by a hard shell coating of sugar solution or dextrose solution.

Cetyl pyridimium chloride may also be used in coating of sugarless gum centers. Like sugar gum centers, the base formulation can be increased in proportion to the amount of coating applied to the center. Formulations with and without cetyl pyridimium chloride similar to those found in previous tables for low and high moisture gum can be used to make gum centers. Generally, the base level may be increased to 30–46% with the other ingredients proportionally reduced. Some typical gum center formulas are in Table 50.

TABLE 50

(WEIGHT PERCENT)

| | EX. 355 | EX. 356 | EX. 357 | EX. 358 | EX. 359 | EX. 360 | EX. 361 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.97 | 45.8 | 40.3 | 44.47 | 41.2 | 25.84 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0$^{a)}$ | 10.0$^{a)}$ |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| CPC$^{b)}$ | —$^{c)}$ | 0.33 | 0.5 | —$^{c)}$ | 0.33 | 0.5 | 0.66$^{d)}$ |

$^{a)}$Lycasin brand hydrogenated starch hydrolyzate used instead of sorbitol liquid.
$^{b)}$This material may be dissolved in water, glycerin, sorbitol liquid, or HSH.
$^{c)}$All of the active agent is in the coating, which comprises 33% of the product.
$^{d)}$This example requires 50% of the product to be a coating with no active agent in the coating, to give a gum product with 0.33% active.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Cetyl pyridimium chloride may be used in sugarless coatings with xylitol, sorbitol, maltitol, lactitol, hydrogenated isomaltulose and erythritol. The following table gives formulas for a xylitol coating:

TABLE 51

(DRY WEIGHT PERCENT)

| | EX. 362 | EX. 363 | EX. 364 | EX. 365 | EX. 366 | EX. 367 |
|---|---|---|---|---|---|---|
| XYLITOL | 94.8 | 92.07 | 89.7 | 90.1 | 89.57 | 87.8 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |

TABLE 51-continued (DRY WEIGHT PERCENT)

| | EX. 362 | EX. 363 | EX. 364 | EX. 365 | EX. 366 | EX. 367 |
|---|---|---|---|---|---|---|
| WAX | 0.1 | 0.1 | 0.1 | 0.1 | 0.1 | 0.1 |
| COLOR | — | — | 1.4 | — | — | — |
| CPC | — | 0.33 | 1.0$^{a}$ | 0.33 | 1.0$^{a}$ | — |

*Lake color dispersed in xylitol solution
**Calcium carbonate used in place of titanium dioxide
$^{a}$All of the active agent is in the coating, which comprises 33% of the product.

The above formulas are used to coat pellets by applying a xylitol/gum arabic solution in multiple coats and air drying. Color or whitener is also mixed in the solution. CPC may be dissolved in water or flavor and added between coating applications, or mixed with the hot syrup and used in the early stages of coating or used throughout the coating process. After pellets have been coated and dried, talc and wax are added to give a polish.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 52

(DRY WEIGHT PERCENT)

| | EX. 368 | EX. 369 | EX. 370 | EX. 371 | EX. 372 | EX. 373 |
|---|---|---|---|---|---|---|
| MALTITOL | 96.8 | 94.57 | 91.1 | 86.8 | 75.77 | 68.5 |
| MALTITOL POWDER | — | — | — | 10.0 | 20.0 | 25.0 |
| ARABINO-GALACTAN | 2.0 | 4.0 | 6.0 | 2.0 | 3.0 | 4.0 |
| FLAVOR | 0.5 | 0.4 | 0.7 | 0.5 | 0.3 | 0.7 |

TABLE 52-continued (DRY WEIGHT PERCENT)

| | EX. 368 | EX. 369 | EX. 370 | EX. 371 | EX. 372 | EX. 373 |
|---|---|---|---|---|---|---|
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| CETYL PYRIDIMIUM CHLORIDE | — | 0.33 | 1.0[a] | — | 0.33 | 1.0[a] |

[a]All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Cetyl pyridimium chloride may be applied in a similar manner as in the previous xylitol coating examples, or preblended with the dry charge materials.

In a similar manner, coatings with sorbitol, lactitol, and hydrogenated isomaltulose may be made in the coating formulas in Table 52 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, erythritol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 53, in which ketoprofen can be added as the active medicament. Ketoprofen is an analgesic to reduce inflammation and pain. These formulas give a 1.5 gram piece containing 12.5 mg of ketoprofen or 0.83% of the total gum product. Gum center formulas may or may not contain encapsulated or controlled release ketoprofen.

TABLE 53

(WEIGHT PERCENT)

| | EX. 374 | EX. 375 | EX. 375 | EX. 377 | EX. 378 | EX. 379 |
|---|---|---|---|---|---|---|
| SUGAR | 52.0 | 48.17 | 46.75 | 44.0 | 40.17 | 37.75 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONOHYDRATE | — | — | — | 10.0 | 10.0 | 10.0 |
| KETOPROFEN | —[a] | 0.83 | 1.25 | —[a] | 0.83 | 1.25 |

[a]All of the active agent is in the coating, which comprises 33% of the product Formulations with or without ketoprofen can also be made similar to those found in previous tables for low, medium, and high moisture formulas. Higher levels of base may be used with a corresponding decrease in other ingredients. Also, other sugars and polyols may be used in the gum center as found in previous tables. Ketoprofen may be added to a gum center only, into a gum coating with none in the center, or to both center and coating.

Ketoprofen can be used in the coating formula on the various pellet gum formulations. The following Table 54 shows some sugar and dextrose type formulas:

TABLE 54

(DRY WEIGHT PERCENT)

| | EX. 380 | EX. 381 | EX. 382 | EX. 383 | EX. 384 | EX. 385 |
|---|---|---|---|---|---|---|
| SUGAR | 97.1 | 94.57 | 91.6 | 96.9 | 94.27 | 91.1 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| KETOPROFEN | — | 0.83 | 2.5[a] | — | 0.83 | 2.5[a] |

| | EX. 386 | EX. 387 | EX. 388 | EX. 389 |
|---|---|---|---|---|
| DEXTROSE MONOHYDRATE | 97.6 | 94.57 | 96.37 | 92.0 |
| GUM ARABIC | 1.5 | 3.0 | 1.5 | 3.0 |
| TITANIUM DIOXIDE | 0.5 | 1.0 | — | — |

TABLE 54-continued (DRY WEIGHT PERCENT)

| | | | | |
|---|---|---|---|---|
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| KETO-PROFEN | — | 0.83 | 0.83 | 2.5[a] |

[a]All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. Ketoprofen may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Ketoprofen may also be premixed with the flavor. Afterthe final coats are applied and dried, wax is applied to give a smooth polish.

The above process gives a hard shell coating. Often a dry charge of powdered sugar or dextrose monohydrate may be used. This gives a somewhat softer coating. A dry charge, which also may contain the active, may be used to build up a coating, but then finished with a straight syrup to obtain a hard shell. Table 55 gives these types of formulas.

TABLE 55

(DRY WEIGHT PERCENT)

| | EX. 390 | EX. 391 | EX. 392 | EX. 393 | EX. 394 | EX. 395 |
|---|---|---|---|---|---|---|
| SUGAR | 76.67 | 78.9 | — | — | 66.67 | — |
| DEXTROSE MONO-HYDRATE | — | — | 76.67 | 83.8 | — | 84.6 |
| POWDER SUGAR* | 20.0 | 15.0 | — | — | — | — |
| POWDER DEXTROSE* | — | — | 20.0 | 10.0 | — | — |

TABLE 55-continued (DRY WEIGHT PERCENT)

| | EX. 390 | EX. 391 | EX. 392 | EX. 393 | EX. 394 | EX. 395 |
|---|---|---|---|---|---|---|
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| KETO-PROFEN | 0.83 | 2.5[a] | 0.83 | 2.5[a] | 0.83 | 2.5[a] |

*Powder and/or crystalline sugar may be used.
[a]All of the active agent is in the coating, which comprises 33% of the product.

In Examples 390–393, gum arabic is blended in the sugar syrup. In Examples 394 and 395, gum arabic powder is dry charged after gum arabic solution is applied in the first stages of coating, then this is followed by a hard shell coating of sugar solution or dextrose solution.

Ketoprofen may also be used in coating of sugarless gum centers. Like sugar gum centers, the base formulation can be increased in proportion to the amount of coating applied to the center. Formulations with and without ketoprofen similar to those found in previous tables for low and high moisture gum can be used to make gum centers. Generally, the base level may be increased to 30–46% with the other ingredients proportionally reduced. Some typical gum formulas are in Table 56.

TABLE 56

(WEIGHT PERCENT)

| | EX. 396 | EX. 397 | EX. 398 | EX. 399 | EX. 400 | EX. 401 | EX. 402 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.47 | 45.05 | 40.3 | 43.97 | 40.45 | 24.83 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| KETOPROFEN[b] | —[c] | 0.83 | 1.25 | —[c] | 0.83 | 1.25 | 1.67[d] |

[a]Lycasin brand hydrogenated starch hydrolyzate used instead of sorbitol liquid.
[b]Ketoprofen may be dissolved in water, glycerin, sorbitol liquid, or HSH, or flavor.
[c]All of the active agent is in the coating, which comprises 33% of the product.
[d]This example requires 50% of the product to be a coating with no active agent in the coating, to give a gum product with 0.83% active agent.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Ketoprofen may be used in sugarless coatings with xylitol, sorbitol, maltitol, lactitol, hydrogenated isomaltulose and erythritol. The following table gives formulas for a xylitol coating:

TABLE 57

(DRY WEIGHT PERCENT)

|  | EX. 403 | EX. 404 | EX. 405 | EX. 406 | EX. 407 | EX. 408 |
|---|---|---|---|---|---|---|
| XYLITOL | 94.8 | 91.57 | 88.2 | 90.1 | 89.07 | 86.3 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| KETO-PROFEN | — | 0.83 | 2.5$^a$ | — | 0.83 | 2.5$^a$ |

*Lake color dispersed in xylitol solution.
Calcium carbonate used in place of titanium dioxide.
$^a$All of the active agent is in the coating, which comprises 33% of the product.

The above formulas are used to coat pellets by applying a xylitol/gum arabic solution in multiple coats and air drying. Color or whitener is also mixed in the solution. After pellets have been coated and dried, talc and wax are added to give a polish. Ketoprofen may be dissolved in water or flavor and added between coating applications, or mixed with the hot syrup and used in the early stages of coating or used throughout the coating process.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 58

(DRY WEIGHT PERCENT)

|  | EX. 409 | EX. 410 | EX. 411 | EX. 412 | EX. 413 | EX. 414 |
|---|---|---|---|---|---|---|
| MALTITOL | 96.8 | 94.07 | 89.6 | 86.8 | 75.27 | 67.0 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| KETO-PROFEN | — | 0.83 | 2.5$^a$ | — | 0.83 | 2.5$^a$ |

$^a$All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Ketoprofen may be applied in a similar manner as in the previous xylitol coating examples, or preblended with the dry charge material and added to the coating.

In a similar manner, coatings with sorbitol, lactitol, and hydrogenated isomaltulose may be made in the coating formulas in Table 58 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, erythritol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 59 in which dextromethorphan hydrobromide can be added as the active medicament. This material is an antitussive for cough relief. These formulas give a 1.5 gram piece containing 15 mg of dextromethorphan hydrobromide or 1.0% of gum product. Gum centers may or may not contain dextromethorphan hydrobromide.

TABLE 59

(WEIGHT PERCENT)

|  | EX. 415 | EX. 416 | EX. 417 | EX. 418 | EX. 419 | EX. 420 |
|---|---|---|---|---|---|---|
| SUGAR | 52.0 | 48.0 | 46.5 | 44.0 | 40.0 | 37.5 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONOHYDRATE | — | — | — | 10.0 | 10.0 | 10.0 |
| DEXTRO-METHORPHAN HBr | —$^a$ | 1.0 | 1.5 | —$^a$ | 1.0 | 1.5 |

Formulations with or without Dextromethorphan HBr can also be made similar to those found previously in Tables for low, medium, and high moisture formulas. Higher levels of base may be used with a corresponding decrease in other ingredients. Also, other sugars and polyols may be used in the gum center as found in previous tables. Dextromethorphan HBr may be added to the gum center only, into a gum coating with none in the center, or both center and coating.

Dextromethorphan HBr can then be used in the coating formula on the various pellet gum formulations. The following Table 60 shows some sugar and dextrose type formulas:

TABLE 60

(DRY WEIGHT PERCENT)

| | EX. 421 | EX. 422 | EX. 423 | EX. 424 | EX. 425 | EX. 426 |
|---|---|---|---|---|---|---|
| SUGAR | 97.1 | 94.4 | 91.1 | 96.9 | 94.1 | 90.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| DEXTRO-METHOR-PHAN HBr | — | 1.0 | 3.0[a] | — | 1.0 | 3.0[a] |

| | EX. 427 | EX. 428 | EX. 429 | EX. 430 |
|---|---|---|---|---|
| DEXTROSE MONO-HYDRATE | 97.6 | 94.4 | 96.2 | 91.5 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| DEXTRO-METHOR-PHAN HBr | — | 1.0 | 1.0 | 3.0[a] |

[a]All of the active agent is in the coating which comprises 33% of the product.

The above formulations are made by making a syrup by dissolving the sugar and gum arabic in solution at about 75% solids at boiling, and suspending titanium dioxide or calcium carbonate in this syrup. Dextromethorphan HBr may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Dextromethorphan HBr may also be premixed with the flavor. After the final coats are applied and dried, wax is applied to give a smooth polish.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. Dextromethorphan HBr may also be added to the dry charge material. Table 61 gives these types of formulas.

TABLE 61

(DRY WEIGHT PERCENT)

| | EX. 431 | EX. 432 | EX. 433 | EX. 434 | EX. 435 | EX. 436 |
|---|---|---|---|---|---|---|
| SUGAR | 76.5 | 78.4 | — | — | 86.5 | — |
| DEXTROSE MONO-HYDRATE | — | — | 76.5 | 83.3 | — | 84.1 |
| POWDER SUGAR* | 20.0 | 15.0 | — | — | — | — |
| POWDER DEXTROSE* | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| DEXTRO-METHOR-PHAN HBr | 1.0 | 3.0[a] | 1.0 | 3.0[a] | 1.0 | 3.0[a] |

*Powder and/or crystalline sugar may be used.
[a]All of the active agent is in the coating, which comprises 33% of the product.

In Examples 431–434 gum arabic is blended in the sugar syrup. In Examples 435 and 436, gum arabic powder is dry charged after a gum arabic solution is applied in the first stages of coating, then this is followed by a hard shell coating of sugar solution or dextrose solution.

Dextromethorphan HBr may also be used in coating of sugarless gum centers. Like sugar gum centers, the base formulation can be increased in proportion to the amount of coating applied to the center. Formulations with and without Dextromethorphan HBr similar to those found in previous tables for low and high moisture gum can be used to make gum centers. Generally, the base level may be increased to 30–46% with the other ingredients proportionally reduced. Some typical gum center formulas are in Table 62.

TABLE 62

(WEIGHT PERCENT)

| | EX. 437 | EX. 438 | EX. 439 | EX. 440 | EX. 441 | EX. 442 | EX. 443 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.3 | 43.3 | 40.3 | 43.8 | 38.7 | 24.5 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a)] | 10.0[a)] |
| FLAVOR | 1.5 | 1.5 | 1.5 | 1.5 | 2.0 | 2.0 | 1.3 |

TABLE 62-continued (WEIGHT PERCENT)

|  | EX. 437 | EX. 438 | EX. 439 | EX. 440 | EX. 441 | EX. 442 | EX. 443 |
|---|---|---|---|---|---|---|---|
| HIGH INTENSITY SWEETENER | 0.2 | 0.2 | 0.2 | 0.2 | 0.2 | 0.3 | 0.2 |
| DEXTROMETHORPHAN HBr[b)] | —[c)] | 1.0 | 3.0 | —[c)] | 1.0 | 3.0 | 2.0[d)] |

[a)]Lycasin brand hydrogenated starch hydrolyzate used instead of sorbitol liquid
[b)]Dextromethorphan HBr may be dissolved in water, glycerin, sorbitol liquid, HSH, or flavor
[c)]All of the active agent is in the coating, which comprises 33% of the product
[d)]This example requires 50% of the product to be a coating with no active agent in the coating, to give a gum product with 1% active agent.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Dextromethorphan may be used in sugarless coatings with xylitol, sorbitol, maltitol, lactitol, hydrogenated isomaltulose and erythritol. The following table gives formulas for a xylitol coating:

TABLE 63

(DRY WEIGHT PERCENT)

|  | EX. 444 | EX. 445 | EX. 446 | EX. 447 | EX. 448 | EX. 449 |
|---|---|---|---|---|---|---|
| XYLITOL | 94.8 | 91.4 | 87.7 | 90.1 | 88.9 | 85.8 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| DEXTROMETHORPHAN HBr | — | 1.0 | 3.0[a] | — | 1.0 | 3.0[a] |

*Lake color dispersed in xylitol solution
**Calcium carbonate used in place of titanium dioxide
[a]All of the active agent is in the coating, which comprises 33% of the product.

The above formulas are used to coat pellets by applying a xylitol/gum arabic solution in multiple coats and air drying. Color or whitener is also mixed in the solution. After pellets have been coated and dried, talc and wax are added to give a polish. Dextromethorphan HBr may be dissolved in water or flavor and added between coating applications, or mixed with hot syrup and used in the early stages of coating or used throughout the coating process.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The active may be premixed with the dry charge material. The following formulations may be used.

TABLE 64

(DRY WEIGHT PERCENT)

|  | EX. 450 | EX. 451 | EX. 452 | EX. 453 | EX. 454 | EX. 455 |
|---|---|---|---|---|---|---|
| MALTITOL | 96.8 | 93.9 | 89.1 | 91.8 | 85.1 | 76.5 |
| MALTITOL POWDER | — | — | — | 5.0 | 10.0 | 15.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| DEXTROMETHORPHAN HBr | — | 1.0 | 3.0[a] | — | 1.0 | 3.0[a] |

[a]All of the active agent is in the coating, which comprises 33% of the product.

Maltitol powder is used to dry charge in the early stages of coating. Maltitol, gum arabic, and whitener is blended into a syrup and applied to pellets. After all coating is applied and dried, talc and wax are added to give a polish. Dextomethorphan may be applied in a similar manner as the previous xylitol examples, or added with the dry charge material.

In a similar manner, coatings with sorbitol, lactitol, and hydrogenated isomaltulose may be made in the coating formulas in Table 64 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, erythritol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

As noted earlier, the gum formulas can be prepared as stick or tab products in the sugar or sugarless type formulations. These formulas can also be made in a pellet or pillow shape pellet or a round ball or any other shape of product for coating/panning. However, gum formulas are generally adjusted to a higher level of gum base to give a more consumer acceptable size of gum bolus.

As a result, gum centers are usually formulated with about 25% to about 40% gum base with a corresponding decrease in the other ingredients except flavor. Generally flavors increase with the level of gum base as the base tends to bind flavors into the gum and more flavor is needed to give a good flavorful product. However flavors can also be added to the coating to give increased flavor impact and more flavor perception.

Some typical sugar type gum center formulations are shown in Table 65 that can be used as centers that are coated with calcium carbonate to give an effective antacid.

TABLE 65

(WEIGHT PERCENT)

| | EX. 456 | EX. 457 | EX. 458 | EX. 459 | EX. 460 | EX. 461 |
|---|---|---|---|---|---|---|
| SUGAR | 48.0 | 48.0 | 46.0 | 40.0 | 39.0 | 36.0 |
| GUM BASE | 30.0 | 35.0 | 40.0 | 30.0 | 35.0 | 40.0 |
| CORN SYRUP | 20.0 | 15.0 | 12.0 | 18.0 | 14.0 | 12.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONOHYDRATE | — | — | — | 10.0 | 10.0 | 10.0 |

Formulations can also be made similar to those found in previous tables for low, medium, and high moisture formulas. Higher levels of base may be used with a corresponding decrease in other ingredients. Also, other sugars may be used in the gum center as found in previous tables.

Calcium carbonate can then be used in the coating formula on the various pellet gum formulations. The following Table 66 shows some sugar and dextrose type formulas: Using a 1 gram center, the levels of calcium carbonate in the following tables will give 250–800 mg per 2 pieces in 1.5–3.0 gum pieces with 33 to 50% coating.

TABLE 66

(DRY WEIGHT PERCENT)

| | EX. 462 | EX. 463 | EX. 464 | EX. 465 | EX. 466 | EX. 467 |
|---|---|---|---|---|---|---|
| SUGAR | 72.1 | 65.4 | 54.1 | 72.4 | 66.1 | 55.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | 25.0 | 30.0 | 40.0 | 25.0 | 30.0 | 40.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |

TABLE 66-continued

| | EX. 468 | EX. 469 | EX. 470 | EX. 471 |
|---|---|---|---|---|
| DEXTROSE MONOHYDRATE | 72.6 | 55.4 | 73.2 | 56.5 |
| GUM ARABIC | 1.5 | 3.0 | 1.5 | 3.0 |
| TITANIUM DIOXIDE | 0.5 | 1.0 | — | — |
| CALCIUM CARBONATE | 25.0 | 40.0 | 25.0 | 40.0 |
| FLAVOR | 0.3 | 0.5 | 0.2 | 0.4 |
| WAX | 0.1 | 0.1 | 0.1 | 0.1 |

The above formulations are made by making a syrup by dissolving the sugar and gum arabic in solution at about 75% solids at boiling, and suspending titanium dioxide and/or calcium carbonate in this syrup. Flavor is not mixed with the hot syrup, but added at low levels with one or more coats. After the final coats are applied and dried, wax is applied to give a smooth polish.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. Table 67 gives these types of formulas.

TABLE 67

(DRY WEIGHT PERCENT)

| | EX. 472 | EX. 473 | EX. 474 | EX. 475 | EX. 476 | EX. 477 |
|---|---|---|---|---|---|---|
| SUGAR | 62.5 | 51.4 | — | — | 52.5 | — |
| DEXTROSE MONOHYDRATE | — | — | 62.5 | 51.3 | — | 42.1 |
| POWDER SUGAR* | 10.0 | 5.0 | — | — | — | — |
| POWDER DEXTROSE* | — | — | 10.0 | 5.0 | 10.0 | 5.0 |
| GUM ARABIC POWDER* | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| CALCIUM CARBONATE | 25.0 | 40.0 | 25.0 | 40.0 | 25.0 | 40.0 |

*Powder and/or crystalline sugar along with gum arabic may be blended with calcium carbonate, or calcium carbonate may be suspended in the sugar or dextrose syrup.

In Examples 472–475, gum arabic is blended in the sugar syrup; In Examples 476 and 477, gum arabic powder is dry charged after a gum arabic solution is applied in the first stages of coating, then this is followed by a hard shell coating of sugar solution or dextrose solution.

Gum arabic may also be used in coating of sugarless gum centers. Like sugar gum centers, the base formulation can be increased in proportion to the amount of coating applied to the center. Formulations similar to those found in previous tables for low and high moisture gum can be used to make gum centers. Generally, the base level may be increased to 30–46% with the other ingredients proportionally reduced. Some typical gum formulas are in Table 68.

TABLE 68

(WEIGHT PERCENT)

| | EX. 478 | EX. 479 | EX. 480 | EX. 481 | EX. 482 | EX. 483 | EX. 484 |
|---|---|---|---|---|---|---|---|
| GUM BASE | 35.0 | 35.0 | 30.0 | 30.0 | 30.0 | 40.0 | 30.0 |
| CALCIUM CARBONATE[b] | — | — | 5.0 | 10.0 | 10.0 | — | — |
| SORBITOL | 43.3 | 45.3 | 46.3 | 40.3 | 49.8 | 41.7 | 46.5 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |

[a]Lycasin brand hydrogenated starch hydrolyzate used instead of sorbitol liquid
[b]This material is base filler and may not release to give an antacid effect.

In the above center formulations, the high intensity sweetener used is aspartame. However other high intensity sweetener such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels similar to those shown previously. The texture may be adjusted by varying glycerin or sorbitol liquid. Sweetness of the center formulation can also be adjusted by varying the level of high intensity sweetener.

Calcium carbonate can be used in sugarless coatings with xylitol, sorbitol, maltitol, lactitol, hydrogenated isomaltulose and erythritol. Gum arabic acts as a binder, film former, hardener of the coated pellet. The following table gives formulas for a xylitol coating:

TABLE 69

(DRY WEIGHT PERCENT)

| | EX. 485 | EX. 486 | EX. 487 | EX. 488 | EX. 489 | EX. 490 |
|---|---|---|---|---|---|---|
| XYLITOL | 69.8 | 52.4 | 65.7 | 50.6 | 65.4 | 49.3 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | — | — | — |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| CALCIUM CARBONATE | 25.0 | 40.0 | 25.0 | 40.0 | 25.0 | 40.0 |

*Lake color dispersed in xylitol solution

The above formulas are used to coat pellets by applying a xylitol/gum arabic solution in multiple coats and air drying. Color or whitener is also mixed in the solution. Calcium carbonate may be suspended in the xylitol hot syrup or added as a dry powder between syrup applications. After pellets have been coated and dried, talc and wax are added to give a polish.

Like xylitol, erythritol coating also requires a binder, film former, and hardener in the coating to make an acceptable product. The following formulations can be made:

TABLE 70

(DRY WEIGHT PERCENT)

| | EX. 491 | EX. 492 | EX. 493 | EX. 494 | EX. 495 | EX. 496 |
|---|---|---|---|---|---|---|
| ERYTHRITOL | 68.8 | 51.5 | 64.2 | 50.1 | 63.4 | 46.8 |
| GUM ARABIC | 5.0 | 7.0 | 8.5 | 8.5 | 10.0 | 12.0 |
| FLAVOR | 0.5 | 0.4 | 0.7 | 0.7 | 0.9 | 0.5 |
| TITANIUM DIOXIDE | 0.5 | 0.9 | — | 0.5 | 0.5 | 0.5 |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4* | — | — | — |
| CALCIUM CARBONATE | 25.0 | 40.0 | 25.0 | 40.0 | 25.0 | 40.0 |

*Lake color dispersed in erythritol solution

The above formulas are used to coat pellets by applying a erythritol/gum arabic solution in multiple coats and air drying. Color or whitener is also mixed in the solution. Calcium carbonate may be suspended in the hot erythritol syrup or added as a dry powder between syrup applications. After pellets have been coated and dried, talc and wax are added to give a polish.

For coating formulas based on sorbitol, maltitol, lactitol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 71

(DRY WEIGHT PERCENT)

| | EX. 497 | EX. 498 | EX. 499 | EX. 500 | EX. 501 | EX. 502 |
|---|---|---|---|---|---|---|
| MALTITOL | 71.8 | 54.9 | 67.1 | 51.8 | 61.1 | 39.5 |
| MALTITOL POWDER | — | — | — | 5.0 | 10.0 | 15.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |

TABLE 71-continued (DRY WEIGHT PERCENT)

|  | EX. 497 | EX. 498 | EX. 499 | EX. 500 | EX. 501 | EX. 502 |
|---|---|---|---|---|---|---|
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| CALCIUM CARBONATE | 25.0 | 40.0 | 25.0 | 40.0 | 25.0 | 40.0 |

Maltitol powder is used to dry charge in the early stages of coating. Maltitol, gum arabic, and whitener is blended into a syrup and applied to pellets. Calcium carbonate may be applied with the syrup suspension, preblended with powder maltitol or added as a dry charge. After all coating is applied and dried, talc and wax are added to give a polish.

In a similar manner, coatings with sorbitol, lactitol, and hydrogenated isomaltulose may be made in the coating formulas in Table 71 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

What is claimed is:

1. A method of producing a chewing gum product containing a physically-modified active agent in order to control the release rate of the active agent comprising the steps of:
   a) mixing a quantity of an active agent, which comprises one or more materials selected from the group consisting of benzoin, glucosamine, grapeseed extract, guarana, phosphotidylserine, phytosterols, phytochemicals, isoflavones, lecithin, lycopene, polyphenol, psyllium, chromium picolinate and phenylpropanolamine, with a modifying agent and a high-potency sweetener selected from the group consisting of neotame, aspartame, alitame, salts of acesulfame, cyclamate and its salts, saccharin and its salts, thaumatin, monellin, dihydrochalcones, sucralose and combinations thereof, to form a modified release rate active agent and high-potency sweetener combination;
   b) adding a quantity of the combination to a chewing gum formulation to provide an effective amount of the active agent in the chewing gum formulation.

2. The method of claim 1 wherein said modifying agent is an encapsulating agent.

3. The method of claim 2 wherein the active agent and encapsulating agent are also mixed with a solvent and the resulting mixture is spray dried prior to being added to the chewing gum.

4. The method of claim 3 wherein the encapsulating agent is selected from the group consisting of maltodextrin and gum arabic.

5. The method of claim 2 wherein the active agent is fluid-bed coated with a solution of encapsulating agent and solvent in order to increase the rate of release of the active agent in the chewing gum.

6. The method of claim 2 wherein the active agent is encapsulated by coacervation in order to decrease the rate of release of active agent in chewing gum.

7. The method of claim 2 wherein the active agent is mixed with a molten encapsulating agent and the active agent is encapsulated by spray chilling in order to decrease the rate of release of the active agent in the chewing gum.

8. The method of claim 2 wherein the active agent is mixed with a polymer as the encapsulating agent and the resulting mixture is extruded into fibers in such a way as to encapsulate the active agent in order to decrease the rate of release of the active agent in the chewing gum.

9. The method of claim 8 wherein the polymer is selected from the group consisting of PVAC, hydroxypropyl cellulose, polyethylene and plastic polymers.

10. The method of claim 1 wherein the active agent is mixed with an absorbent as the modifying agent.

11. The method of claim 1 wherein another active agent is added to the chewing gum formulation.

12. The method of claim 11 wherein the other active agent has been treated to modify its release rate from the chewing gum.

13. A chewing gum product made according to the method of claim 1.

14. The method of claim 1 wherein the effective amount of active agent in the chewing gum formulation is from about 0.2% to about 5% in the chewing gum product.

15. A method of producing a chewing gum containing a physically-modified active agent in order to control the release rate of the active agent comprising the steps of:
   a) mixing a quantity of the active agent, which comprises one or more materials selected from the group consisting of benzoin, glucosamine, grapeseed extract, quarana, phosphotidylserine, phytosterols, phytochemicals, isoflavones, lecithin, lycopene, polyphenol, psyllium, chromium picolinate and phenylpropanolamine, with a high-potency sweetener selected from the group consisting of neotame, aspartame, alitame, salts of acesulfame, cyclamate and its salts, saccharin and its salts, thaumatin, monellin, dihydrochalcones, sucralose and combinations thereof, and an agglomerating agent and solvent to partially coat the active agent, agglomerating agent and high-potency sweetener;

b) removing the solvent from the mixture of active agent, high-potency sweetener and agglomerating agent to form a dried material; and c) adding a quantity of the dried material to a chewing gum formulation to provide an effective amount of the active agent in the gum.

16. The method of claim 1 wherein the dried material is ground to a powder prior to adding the dried material to the chewing gum.

17. A chewing gum product made according to the method of claim 15.

18. The method of claim 15 wherein the effective amount of active agent in the chewing gum formulation is from about 0.2% to about 5% in the chewing gum product.

19. A method of producing a chewing gum product containing an active agent, which comprises one or more materials selected from the group consisting of benzoin, glucosamine, grapeseed extract, guarana, phosphotidylserine, phytosterols, phytochemicals, isoflavones, lycopene, polyphenol, psyllium, chromium picolinate and phenylpropanolamine, wherein the active agent is a part of a rolling compound applied on the chewing gum product.

20. A chewing gum product made according to the method of claim 19.

21. A method of producing a chewing gum product containing an active agent, which comprises one or more materials selected from the group consisting of benzoin, glucosamine, grapeseed extract, guarana, phosphotidylserine, phytosterols, phytochemicals, isoflavones, lycopene, polyphenol, psyllium, chromium picolinate and phenylpropanolamine, wherein the active agent is part of the liquid in a liquid-center chewing gum product.

22. A chewing gum product made according to the method of claim 21.

23. A method of producing a chewing gum product containing an absorption-enhanced active agent in order to control the absorption rate of the active agent comprising the steps of:

a) mixing a quantity of the active agent, which comprises one or more materials selected from the group consisting of nutraceuticals and nutritional supplements, with an absorption enhancing agent selected from the group consisting of ethanol, polytheylene glycol, 2-pyrrolidones, myristic acid, p-phenyl phenol, nitrobenzene, stearyl alcohol, cetyl alcohol, croton oil, liquid paraffin, dimethyl sulfoxide, non-ionic surfactants, liposomes, lecithin fractions, long chain amphipathic molecules and mixtures thereof; and b) incorporating a quantity of the mixture into a chewing gum formulation to provide an active agent level in the chewing gum formulation of from about 12 micrograms to about 250 milligrams per gram of chewing gum product.

24. A chewing gum product made according to the method of claim 23.

25. A coated chewing gum product containing an active agent comprising a compound selected from the group consisting of capsicum, chamomile, cat's claw, echinacea, garlic, ginger, green tea, golden seal, kava kava, nettle, passion flower, saw palmetto, St. John's wort, valerian, benzoin, glucosamine, grapeseed extract, guarana, phosphotidylserine, phytosterols, phytochemicals, isoflavones, lycopene, polyphenol, psyllium, chromium picolinate, phenylpropanolamine and mixtures thereof, wherein the active agent is a part of a coating on a chewing gum pellet.

26. A method of producing coated chewing gum products containing at least one active agent in the coating, the active agent comprising a compound selected from the group consisting of capsicum, chamomile, cat's claw, echinacea, garlic, ginger, green tea, golden seal, kava kava, nettle, passion flower, saw palmetto, St. John's wort, valerian, benzoin, glucosamine, grapeseed extract, guarana, phosphotidylserine, phytosterols, phytochemicals, isoflavones, lycopene, polyphenol, psyllium, chromium picolinate, phenylpropanolamine and mixtures thereof, comprising the steps of:

a) providing chewing gum product cores:

b) providing a coating solution;

c) coating the chewing gum product cores with the coating solution to provide coated chewing gum products, the coating including the active agent at a level of from about 12 micrograms to about 250 milligrams per gram of coated chewing gum product.

27. The method of claim 26 wherein the active agent is mixed in the coating solution prior to coating the cores.

28. The method of claim 27 wherein the active agent is also mixed with a solvent before adding to the coating solution and the resulting mixture is added to the chewing gum coating.

29. The method of claim 28 wherein the solvent is water, alcohol or flavor.

30. The method in claim 26 wherein a high-potency sweetener selected from the group consisting of aspartame, alitame, salts of acesulfame, cyclamate and its salts, saccharine and its salts, neotame, thaumatin, monellin, dihydrochalcones, sucralose and combinations thereof is mixed in the coating solution.

31. The method of claim 26 wherein the coating operation includes the application of multiple coats of coating solution and application of powder material between coats of coating solution.

32. The method of claim 31 wherein the active agent is included in the powder material.

33. The method of claim 31 wherein an active agent is included in both the coating solution and the powder material.

34. The method of claim 26 wherein an active agent is also included in the chewing gum cores.

35. The method of claim 34 wherein the active agents in the gum cores and coating are the same.

36. The method of claim 34 wherein the active agent in the cores is different than the active agent in the coating.

37. The method of claim 34 wherein at least one of the active agents in the coating and in the cores is treated with a modifying agent to control the release of the active agent prior to being incorporated into the coating or into the cores.

38. The method of claim 26 wherein at least two different coating solutions are used to make the coating.

39. The method of claim 38 wherein the active agent is mixed with the first of the at least two different coating solutions and applied to the cores with the first coating solution to form a film, and a second coating solution without an active agent is applied over the film coated cores.

40. The method of claim 26 wherein the active agent in the coating has been treated with a modifying agent to control its release prior to being used in the coating.

41. A method of producing coated chewing gum products containing at least one active agent in the coating the active agent comprising a compound selected from the group consisting of capsicum, chamomile, cat's claw, echinacea, garlic, ginger, green tea, golden seal, kava kava, nettle, passion flower, saw palmetto, St. John's wort, valerian, benzoin, glucosamine, grapeseed extract, guarana, phosphotidylserine, phytosterols, phytochemicals, isoflavones, lycopene, polyphenol, psyllium, chromium picolinate, phenylpropanolamine and mixtures thereof, comprising the steps of:

a) providing chewing gum product cores:

b) providing a coating solution;

c) coating the chewing gum product cores with the coating solution to provide coated chewing gum products, the coating including the active agent at a level of from about 0.2% to about 5% in the gum products.

42. A method of producing coated chewing gum products containing at least one active agent in the coating treated so as to modify the absorption of the active agent in the mouth, the active agent comprising a compound selected from the group consisting of capsicum, chamomile, cat's claw, echinacea, garlic, ginger, ginko, ginseng, green tea, golden seal, kava kava, nettle, passion flower, saw palmetto, St. John's wort, valerian, benzoin, glucosamine, grapeseed extract, guarana, phosphotidylserine, phytosterols, phytochemicals, isoflavones, lecithin, lycopene, polyphenol, psyllium, chromium picolinate, phenylpropanolamine and mixtures thereof, comprising the steps of:

a) providing chewing gum product cores:

b) providing a coating solution;

c) coating the chewing gum product cores with the coating solution to provide coated chewing gum products, the coating including the active agent at a level of from about 12 micrograms to about 250 milligrams per gram of coated chewing gum product and an absorption enhancing agent selected from the group consisting of ethanol, polytheylene glycol, 2-pyrrolidones, myristic acid, p-phenyl phenol, nitrobenzene, stearyl alcohol, cetyl alcohol, croton oil, liquid paraffin, dimethyl sulfoxide, non-ionic surfactants, liposomes, lecithin fractions, and long chain amphipathic molecules and mixtures thereof.

* * * * *

UNITED STATES PATENT AND TRADEMARK OFFICE
CERTIFICATE OF CORRECTION

PATENT NO. : 6,949,264 B1  
DATED : September 27, 2005  
INVENTOR(S) : Gordon N. McGrew et al.

Page 1 of 1

It is certified that error appears in the above-identified patent and that said Letters Patent is hereby corrected as shown below:

Title page,  
Item [75], Inventors, delete "David G. Barkalow, Deerfield, IL (US);Jack D. Nimz, Wauconda, IL (US); Steven E. Zibell, Tinley Park, IL (US); Rebecca A. Aumann, Chicago, IL (US); Daniel J. Zyck, North Riverside, IL (US); Daniel J. Sitler, Woodridge, IL (US); Jeffrey S. Hook, Lockport, IL (US); James R. Maxwell, Chicago, IL (US); Michael A. Reed, Merrillville, IN (US); Victor V. Gudas, Oak Lawn, IL (US); Philip G. Schnell, Downers Grove, IL (US); Henry T. Tyrpin, Palos Park, IL (US); Michael P. Russell, Evergreen Park, IL (US); Donald J. Townsend, Moores Hill, IN (US); Donald A. Seielstad, Frankfurt, IL (US); Ronald L. Ream, Plano, IL (US); Christine L. Corriveau, Orland Park, IL (US); William J. Wokas, Bolingbrook, IL (US); Thomas M. Tongue, Joliet, IL (US)".

Column 76,  
Line 8, after "guarana," insert -- inulin, --.  
Line 9, after "isoflavones," delete "lecithin,".  
Line 67, delete "prapeseed" and substitute -- grapeseed --.

Column 77,  
Line 1, delete "quarana," and substitute -- guarana, --.  
Line 2, after "isoflavones," delete "lecithin,".  
Line 18, delete "claim 1" and substitute -- claim 15 --.  
Line 30, after "phytosterols," delete "phytochemicals,".  
Line 32, before "the active" delete "wherein" and substitute -- including applying --.  
Line 33, after "agent" delete "is a" and substitute -- as --; and after "compound" delete "applied on" and substitute -- onto --.  
Line 43, before "the active" delete "wherein" and substitute -- comprising including --.  
Line 44, after "agent" delete "is" and substitute -- as --.

Signed and Sealed this

Fourteenth Day of March, 2006

JON W. DUDAS  
*Director of the United States Patent and Trademark Office*